US012293512B2

United States Patent
Shiba et al.

(10) Patent No.: US 12,293,512 B2
(45) Date of Patent: May 6, 2025

(54) OPHTHALMIC IMAGE PROCESSING DEVICE AND OPHTHALMIC IMAGE PROCESSING METHOD

(71) Applicant: NIDEK CO., LTD., Aichi (JP)

(72) Inventors: Ryosuke Shiba, Aichi (JP); Yoshiki Kumagai, Aichi (JP)

(73) Assignee: NIDEK CO., LTD., Aichi (JP)

( * ) Notice: Subject to any disclaimer, the term of this patent is extended or adjusted under 35 U.S.C. 154(b) by 466 days.

(21) Appl. No.: 17/528,848

(22) Filed: Nov. 17, 2021

(65) Prior Publication Data

US 2022/0164949 A1    May 26, 2022

(30) Foreign Application Priority Data

Nov. 20, 2020    (JP) .................................. 2020-193429

(51) Int. Cl.
*G06T 7/00*    (2017.01)
*A61B 3/10*    (2006.01)
(Continued)

(52) U.S. Cl.
CPC ............ *G06T 7/0012* (2013.01); *A61B 3/102* (2013.01); *G06N 20/00* (2019.01); *G06T 11/00* (2013.01);
(Continued)

(58) Field of Classification Search
CPC .......... A61B 3/102; G06T 2207/10101; G06T 2207/30041; G06T 7/0012; G06T 2210/41
See application file for complete search history.

(56) References Cited

U.S. PATENT DOCUMENTS

RE49,023 E    4/2022    Isogai et al.
RE49,024 E    4/2022    Isogai et al.
(Continued)

FOREIGN PATENT DOCUMENTS

JP    2012-161426 A    8/2012
JP    2016-129664 A    7/2016
(Continued)

OTHER PUBLICATIONS

Communication issued on May 28, 2024 by the Japan Patent Office for Japanese Patent Application No. 2020-193429.
(Continued)

*Primary Examiner* — Wassim Mahrouka
(74) *Attorney, Agent, or Firm* — Sughrue Mion, PLLC

(57) ABSTRACT

An ophthalmic image processing device processes an ophthalmic image of a subject eye. The ophthalmic image processing device includes a controller which acquires an ophthalmic image including a tomographic image of a plurality of tomographic planes in a subject eye, acquires a probability distribution for identifying two or more tissues included in a plurality of tissues in the tomographic image, by inputting the ophthalmic image into a mathematical model trained with using a machine learning algorithm, generates a structural abnormality degree map showing a two-dimensional distribution of a degree of abnormality of a structure in the tissue, for each of the two or more tissues, based on the probability distribution, and simultaneously displays two or more structural abnormality degree maps generated for each of the two or more tissues side by side on a display device.

10 Claims, 9 Drawing Sheets

(51) Int. Cl.
  *G06N 20/00* (2019.01)
  *G06T 11/00* (2006.01)
(52) U.S. Cl.
  CPC .............. *G06T 2207/10101* (2013.01); *G06T 2207/20076* (2013.01); *G06T 2207/20081* (2013.01); *G06T 2207/30041* (2013.01); *G06T 2207/30101* (2013.01); *G06T 2210/41* (2013.01)

(56) References Cited

U.S. PATENT DOCUMENTS

| | | |
|---|---|---|
| 2011/0170062 A1 | 7/2011 | Isogai et al. |
| 2012/0127428 A1 | 5/2012 | Isogai et al. |
| 2012/0130270 A1* | 5/2012 | Imamura .................. A61B 3/12 600/558 |
| 2018/0003479 A1 | 1/2018 | Tomatsu et al. |
| 2018/0116501 A1 | 5/2018 | Akiba et al. |
| 2019/0139214 A1* | 5/2019 | Trenholm .......... G01B 9/02083 |
| 2019/0272631 A1* | 9/2019 | Shemonski ............ A61B 3/102 |
| 2020/0069175 A1 | 3/2020 | Kumagai et al. |
| 2020/0196856 A1 | 6/2020 | Kim et al. |
| 2020/0245858 A1 | 8/2020 | Takeno et al. |
| 2021/0224997 A1 | 7/2021 | Kushida et al. |
| 2021/0295508 A1 | 9/2021 | Shiba et al. |
| 2023/0210359 A1 | 7/2023 | Takeno et al. |

FOREIGN PATENT DOCUMENTS

| | | |
|---|---|---|
| JP | 2016-198447 A | 12/2016 |
| JP | 2018-121886 A | 8/2018 |
| JP | 2020-18794 A | 2/2020 |
| JP | 2020-58800 A | 4/2020 |
| JP | 2020-110581 A | 7/2020 |
| JP | 2020-121038 A | 8/2020 |

OTHER PUBLICATIONS

Communication dated Oct. 22, 2024, issued by the Japanese Patent Office in Japanese Application No. 2020-193429.
Communication dated Mar. 4, 2025, issued by the Japanese Patent Office in Japanese Application No. 2020-193429.

* cited by examiner

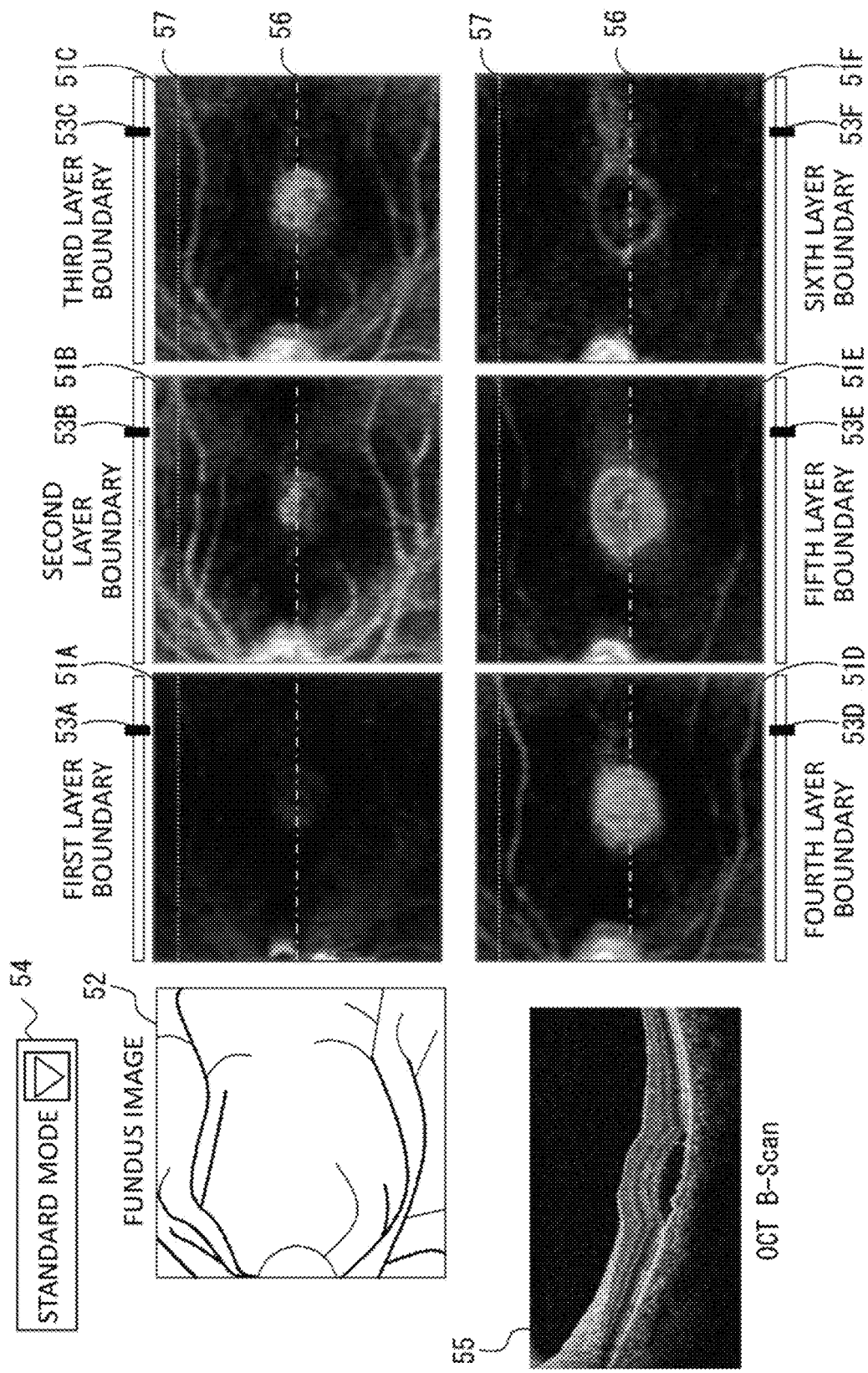

OPHTHALMIC IMAGE PROCESSING DEVICE AND OPHTHALMIC IMAGE PROCESSING METHOD

CROSS-REFERENCE TO RELATED APPLICATION

This application claims priority from Japanese Patent Application No. 2020-193429 filed on Nov. 20, 2020, the entire subject-matter of which is incorporated herein by reference.

TECHNICAL FIELD

The present disclosure relates to an ophthalmic image processing device that processes an ophthalmic image of a subject eye and an ophthalmic image processing method that is executed in the ophthalmic image processing device.

BACKGROUND

In the related art, various techniques for estimating abnormalities of a structure of an object shown in an image or the like have been proposed.

For example, in JP-A-2020-18794 by an inventor of the present application, a method using a learned model, in which a probability distribution for identifying a tissue in an ophthalmic image is acquired by inputting an ophthalmic image, has been proposed. According to JP-A-2020-18794, a quantitative degree of abnormality of a structure is obtained based on the probability distribution output from the learned model.

Further, JP-A-2020-18794 also discloses the generation of a structural abnormality degree map showing a two-dimensional distribution of a degree of abnormality of the structure in the tissue. JP-A-2020-18794 discloses the generation of the structural abnormality degree map for the entire tissue, or for any specific layer or boundary regarding the tissue including a plurality of layers and boundaries.

However, using one structural abnormality degree map for the entire tissue or any specific tissue, it is possible to recognize the presence or absence of the abnormality, but it is difficult to recognize the whole picture of the structural abnormality.

SUMMARY

A typical object of the present disclosure is to provide an ophthalmic image processing device and an ophthalmic image processing method capable of allowing a user to appropriately determine an abnormality of a structure of a tissue shown in an ophthalmic image.

An ophthalmic image processing device that processes an ophthalmic image of a subject eye, including:
  a controller configured to:
    acquire an ophthalmic image including a tomographic image of a plurality of tomographic planes in a subject eye;
    acquire a probability distribution for identifying two or more tissues included in a plurality of tissues in the tomographic image, by inputting the ophthalmic image into a mathematical model trained with using a machine learning algorithm;
    generate a structural abnormality degree map showing a two-dimensional distribution of a degree of abnormality of a structure in the tissue, for each of the two or more tissues, based on the probability distribution; and
    simultaneously display two or more structural abnormality degree maps generated for each of the two or more tissues side by side on a display device.

An ophthalmic image processing method executed by an ophthalmic image processing device that processes an ophthalmic image of a subject eye, in which an ophthalmic image processing program is executed by a controller of the ophthalmic image processing device to cause the ophthalmic image processing device to execute:
  an image acquisition step of acquiring an ophthalmic image including a tomographic image of a plurality of tomographic planes in a subject eye as an ophthalmic image captured by an ophthalmic image capturing device;
  an acquisition step of acquiring a probability distribution for identifying two or more tissues included in a plurality of tissues in the tomographic image, by inputting the ophthalmic image into a mathematical model trained with using a machine learning algorithm;
  a structural abnormality degree map generation step of generating a structural abnormality degree map showing a two-dimensional distribution of a degree of abnormality of a structure in the tissue, for each of the two or more tissues, based on the probability distribution; and
  a display step of simultaneously displaying two or more structural abnormality degree maps generated for each of the two or more tissues side by side on a display device.

According to the ophthalmic image processing device and the ophthalmic image processing method described in the present disclosure, it is possible for a user to more appropriately determine an abnormality of a structure of a tissue shown in an ophthalmic image.

BRIEF DESCRIPTION OF DRAWINGS

FIG. 11 is a diagram illustrating an example of a display mode of a plurality of structural abnormality degree maps generated for each boundary.

DETAILED DESCRIPTION

Outline

Figure 1:
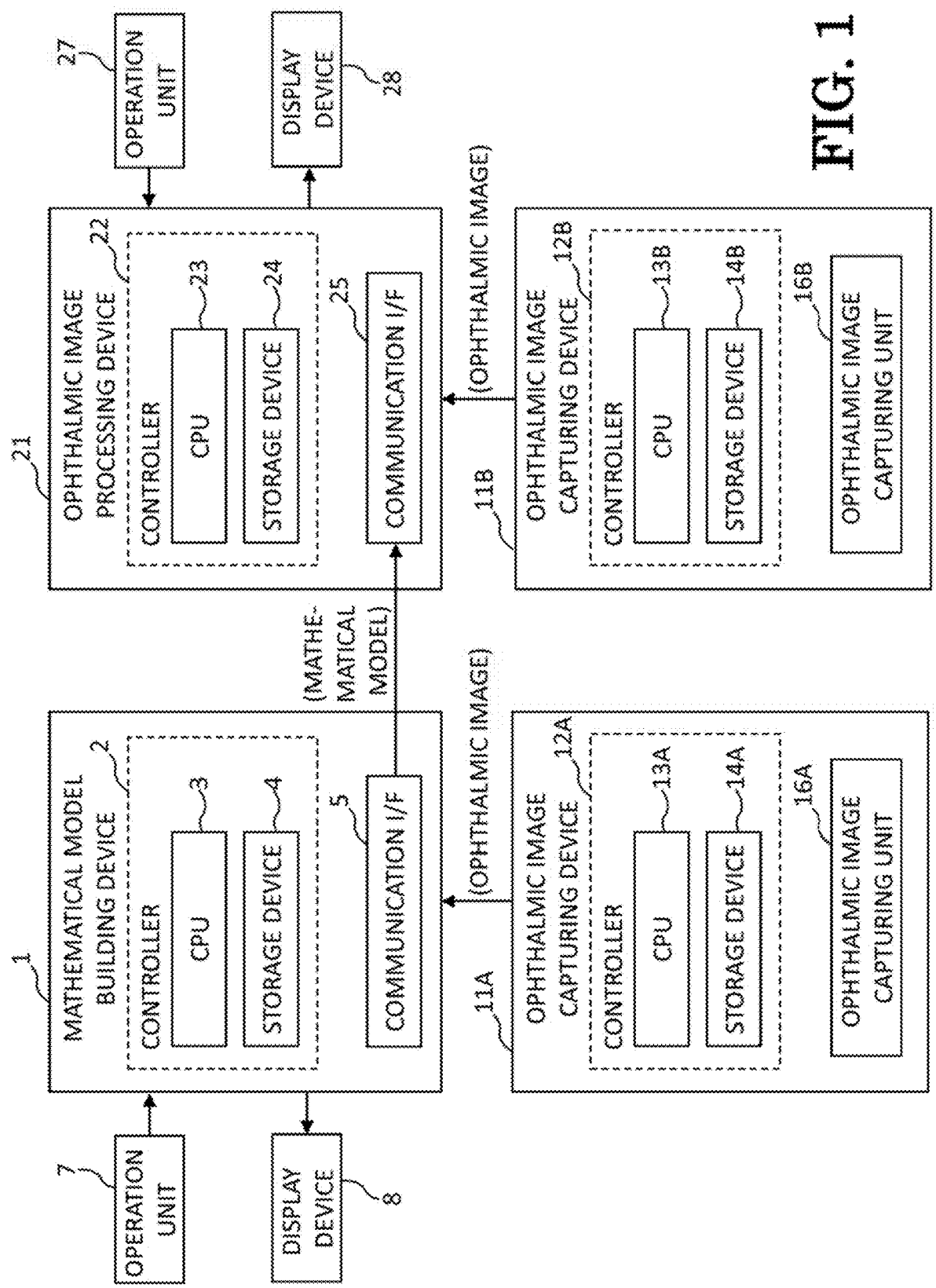
FIG. 1 is a block diagram illustrating a schematic configuration of a mathematical model building device 1, an ophthalmic image processing device 21, and ophthalmic image capturing devices 11A and 11B.

An exemplary embodiment of the present disclosure will be described below. In the present embodiment, a method of generating and displaying a structural abnormality degree map from an ophthalmic image will be mainly described.

In the present embodiment, an ophthalmic image is processed by an ophthalmic image processing device. A controller of the ophthalmic image processing device acquires an ophthalmic image including a tomographic image of a plurality of tomographic planes in a subject eye. The controller acquires a probability distribution for identifying two or more tissues included in a plurality of tissues in the tomographic image by inputting the ophthalmic image into a mathematical model trained with using a machine learning algorithm. The controller generates a structural abnormality degree map showing a two-dimensional distribution of a degree of abnormality of a structure in the tissue for each of the two or more tissues based on the probability distribution. The controller simultaneously displays two or more structural abnormality degree maps generated for each of the two or more tissues side by side on a display device.

On each of the structural abnormality degree maps, a site where the structural abnormality occurs in each of the tissues, is visualized. The user can accurately recognize the degree of abnormality of the structure at each position in the two-dimensional area by the structural abnormality degree map. Furthermore, by using the two or more structural abnormality degree maps generated for each of the two or more tissues simultaneously displayed side by side on the display device, the distribution and spread of the structural abnormality in the depth direction can be seen. Therefore, the simultaneous display of two or more structural abnormality degree maps generated for each of two or more tissues is useful for the user to quickly recognize the whole picture of the structural abnormality.

Note that, the plurality of tissues identified by the mathematical model may be present at different positions with each other with respect to the depth direction (z direction) of the subject eye. As an example, of the plurality of layers and boundaries of the layers in a fundus, two or more layers or boundaries may be identified by the mathematical model.

In the present embodiment, the ophthalmic image including the tomographic image of the plurality of tomographic planes in the subject eye is acquired and further processed by the controller. The positions of the plurality of tomographic planes are different from each other in the subject eye. In the following description, unless otherwise specified, the tomographic plane is a plane that extends in the XZ direction. However, it is not necessarily limited to this. Each of the tomographic images may be, for example, an OCT image captured by an OCT device. At this time, the OCT image may be a two-dimensional OCT image or a three-dimensional OCT image. Further, the tomographic image may be a motion contrast image (hereinafter, it is referred to as an MC image). The MC image is created by using the motion contrast data obtained by processing a plurality of OCT data acquired from the same position at different times. The tomographic image is not necessarily limited to the OCT image and may be captured by a device other than the OCT device (for example, a scheimpflug camera or the like).

The mathematical model may be trained with using a training data set in which data of the tomographic image of the tissue of the subject eye that is captured ago is used for the input side, and data indicating the tissue in the tomographic image of the input side is used for the output side. In this case, the trained mathematical model can appropriately output the probability distribution for identifying the tissue by inputting the tomographic image.

Note that, a specific aspect of the mathematical model that outputs the probability distribution can be appropriately selected. For example, the mathematical model may output the probability distribution having the coordinates, where at least one of the specific boundary and the specific site of the tissue exists in the area of the input tomographic image, as a probability variable. In this case, at least one of the boundary and the specific site in the tomographic image is appropriately and directly identified based on the probability distribution output by the mathematical model. Note that in this case, a "specific boundary" that is a target for acquiring the probability distribution may be one boundary or a plurality of boundaries. When acquiring the probability distribution of a plurality of boundaries, the controller may acquire the probability distributions of each of the plurality of boundaries separately. Similarly, the number of the "specific sites" that are targets for acquiring the probability distribution may be one or plural. Further, the area in the ophthalmic image as a unit for acquiring the probability distribution may be any of a one-dimensional area, a two-dimensional area, and a three-dimensional area. The dimension of the coordinates used as a probability variable may match the dimension of the area that is the unit for acquiring the probability distribution.

Based on the acquired probability distribution, structural information indicating the degree of abnormality of the structure in the tissue can be obtained. As a two-dimensional map of the structural information, the structural abnormality degree map showing the two-dimensional distribution of the degree of abnormality of the structure in the tissue may be generated.

The structural information may be, for example, the degree of divergence of the acquired probability distribution with respect to the probability distribution output in a case where the tissue is accurately identified. The degree of divergence may include the entropy (the average amount of information) of the acquired probability distribution. The entropy represents the degree of uncertainty, messiness, and disorder. In the present disclosure, the entropy of the probability distribution output in the case where the tissue is accurately identified is zero. Further, the entropy increases as the degree of abnormality of the structure in the tissue increases and it becomes difficult to identify the tissue. Therefore, by using the entropy of the probability distribution as the degree of divergence, the degree of abnormality of the structure in the tissue is more appropriately quantified. However, a value other than entropy may be adopted as the degree of divergence. For example, at least one of the standard deviation, the coefficient of variation, the variance, and the like indicating the degree of dispersion of the acquired probability distribution may be used as the degree of divergence. The KL divergence or the like, which is a measure for measuring the difference between probability distributions, may be used as the degree of divergence. Further, the maximum value of the acquired probability distribution may be used as the degree of divergence.

Such the degree of divergence may be calculated by the controller based on the probability distribution output by the mathematical model. Further, the conversion from the probability distribution to the degree of divergence is performed in the mathematical model, and the degree of divergence may be acquired as an output from the mathematical model. Further, the structural abnormality degree map may be generated in the mathematical model, and the structural abnormality degree map may be acquired as the output from the mathematical model.

Modification Example of Structural Abnormality Degree Map: Difference Map

Note that, in the fundus, it is known that the fovea, the optic disc, and the like are significantly different in structure from other areas in the fundus. Therefore, even with a normal eye, the tissues of the fovea and the optic disc tend to have a higher degree of divergence in the structure as compared with the other tissues. Therefore, when the two-dimensional distribution of the degree of divergence is represented as the structural abnormality degree map, the area of the fovea and the optic disc can be depicted as an area having a higher degree of abnormality as compared with the other areas on the structural abnormality degree map in the fundus even in the normal eye. In this case, the area, which has the higher degree of abnormality of the structure corresponding to at least one of the fovea and the optic disc, can be utilized as a marker for the user to recognize a positional relationship on the structural abnormality degree map. On the other hand, even when an abnormality actually occurs in either the fovea or the optic disc, it is difficult for the user to recognize the abnormality from the structural abnormality degree map represented by using the two-dimensional distribution of the degree of divergence. In contrast to this, the structural abnormality degree map may be a difference map based on the two-dimensional distribution of the degree of divergence in the subject eye and the two-dimensional distribution of the degree of divergence in the normal eye. The two-dimensional distribution of the degree of divergence in the normal eye may be created by collecting a plurality of tomographic images in the normal eye. In this case, as compared with the structural abnormality degree map represented as the two-dimensional distribution of the degree of divergence, in the difference map, it is considered that the degree of abnormality of the structure in and around the tissues of the fovea, the optic disc, and the like that originally tend to have a high degree of divergence, is more likely to be reflected on the map more appropriately. Note that, in the fundus, the tissue, which originally tends to have a high degree of divergence in addition to the tissues of the fovea and the optic disc, includes a blood vessel described below, and in the difference map, it can be reduced that a position of the blood vessel is represented as a place having a high degree of abnormality with respect to the surroundings regardless of whether or not the structural abnormality actually occurs.

Setting Correspondence Relationship Between Degree of Abnormality of Structure and Gradation Value for Each Tissue Each pixel included in the structural abnormality degree map may be represented by a gradation value according to the degree of abnormality of the structure. For example, in the tomographic image, the blood vessel is depicted in a manner different from that of surrounding tissues, so that the degree of abnormality of the structure tends to be higher with respect to that of surrounding tissues. Therefore, even in the normal eye, in the tissues in which a large number of blood vessels are distributed, areas, where a larger degree of abnormality of the structure is output, are more likely to be distributed at more positions as compared with the tissues in which a small number of blood vessels are distributed. Therefore, there is a large difference in the degree of noise represented as a place with a high degree of abnormality with respect to the surroundings regardless of whether or not the structural abnormality actually occurs between the structural abnormality degree maps of each of the tissues. In a case where the plurality of structural abnormality degree maps are simultaneously displayed with large differences in the degree of noise, for example, in a case where the correspondence relationships between the degree of abnormality of the structure and the gradation value are the same and aligned between the structural abnormality degree maps for each of the tissues when the difference in the degree of noise between the structural abnormality degree maps represents the difference in the degree of abnormality between the tissues, there is a possibility that it is easily misunderstood by the user.

In contrast to this, in the present embodiment, the correspondence relationship between the degree of abnormality of the structure in the structural abnormality degree map and the gradation value of each pixel may be changeable for each tissue between the two or more structural abnormality degree maps generated for each of two or more tissues. Alternatively, the correspondence relationship between the degree of abnormality of the structure and the gradation value of each pixel in the structural abnormality degree map may differ according to the tissue. Note that, the correspondence relationship between the degree of abnormality of the structure and the gradation value of each pixel may have the gamma characteristics for converting the degree of abnormality of the structure into the gradation value. The gamma characteristics can be represented as, for example, a gamma value. As an example, the correspondence relationship between the degree of abnormality of the structure and the gradation value can be represented by using the following Equation 1. "input" is the degree of abnormality of the structure, and "output" is the gradation value. "$\gamma$" is the gamma value.

$$\text{output} = \text{input}^{1/\gamma} \qquad \text{(Equation 1)}$$

Note that, "input" is normalized in advance with a value in a range of 0 to 1. In this case, after the calculation of Equation 1, integer conversion is appropriately performed so as to obtain a gradation representation at the desired stage. For example, by multiplying "output" obtained in Equation 1 by 255, it may be imaged with 256 gradations.

For convenience, of the two or more structural abnormality degree maps, the structural abnormality degree map in the tissue in which a relatively large number of blood vessels are distributed is referred to as a first structural abnormality degree map. Further, a structural abnormality degree map in the tissues having a relatively small number of blood vessels with respect to the first structural abnormality degree map is referred to as a second structural abnormality degree map.

For example, in a case where the gamma value in the first structural abnormality degree map is smaller than that of the second structural abnormality degree map when the first structural abnormality degree map and the second structural abnormality degree map are compared, the difference in the degree of noise between the structural abnormality degree maps is less conspicuous. Therefore, the above-mentioned misunderstanding is less likely to occur. As a result, the abnormality of the structure in each of the tissues can be easily recognized appropriately by the user based on the structural abnormality degree map for each tissue.

For example, it is known that the blood vessels are concentrated on the superficial layer side among the plurality of tissues included in the fundus. Therefore, for example, the appropriate gamma characteristics for each of the tissues may be individually determined in advance for each tissue (here, for each layer or each layer boundary).

Further, when it is desired to check a subtle abnormality of the structure in any tissue, the gamma value of the structural abnormality degree map in the desired tissue may be increased based on the operation of the user. As a result, the subtle abnormality of the structure in the desired tissue is highlighted in the structural abnormality degree map so that the abnormality of the structure can be easily checked by the user.

Further, the tissue in which a characteristic abnormality of the structure occurs may differ according to the type of disease. Therefore, the correspondence relationship between the degree of abnormality of the structure and the gradation value of each pixel for each tissue may be settable, for example, according to the type of disease. The type of disease may be appropriately selectable. For example, the user may manually input either the case name, the disease name, or the like to the device so that the type of the disease may be selected according to the input. As a result, the characteristic abnormality of the structure for each disease can be easily checked by the user via the structural abnormality degree map. Note that, the gamma correction does not necessarily have to be utilized to set or change the correspondence relationship between the degree of abnormality of the structure and the gradation value for each of the structural abnormality degree map. For example, at least one of the brightness and contrast of each of the structural abnormality degree maps may be set or changed for each of the structural abnormality degree maps. Further, processing such as a histogram flattening or the like may be performed with respect to any structural abnormality degree map.

Further, the correspondence relationship between the degree of abnormality of the structure and the gradation value in each of the structural abnormality degree maps may be adjusted according to a noise level of the ophthalmic image (here, the tomographic image). The degree of divergence may also be high when a tomographic image with poor image quality is processed. Therefore, when the noise level of the ophthalmic image is high, a noisy structural abnormality degree map is likely to be output. Note that, the noise level of the ophthalmic image may be an evaluation value with respect to the tomographic image included in the ophthalmic image. In this case, for example, the gamma correction may be automatically performed for each structural abnormality degree map according to the noise level for each tissue in the ophthalmic image. Further, for example, it may be an evaluation value with respect to the front image generated for each tissue (for example, an OCT en-face image for each tissue). For example, as the evaluation value, the strength of the signal of the ophthalmic image or an index (for example, SSI (Signal Strength Index) or QI (Quality Index), or the like) indicating the goodness of the signal can be utilized.

Simultaneous Display of Front Image of Subject Eye and Structural Abnormality Degree Map In the present embodiment, the controller of the ophthalmic image processing device may further acquire a front image of the subject eye corresponding to the structural abnormality degree map. In other words, the front image of the site of the subject eye, including the tissue indicated by the structural abnormality degree map, may be acquired. The controller may display the acquired front image on a display device together with the structural abnormality degree map. As a result, it becomes easier for the user to recognize the position on the subject eye for the area having a high degree of abnormality on the structural abnormality degree map. Note that at this time, two or more structural abnormality degree maps corresponding to the two or more tissues may be simultaneously displayed. The front image corresponding to at least one of two or more structural abnormality degree maps may be displayed on the display device. Further, the front image may be displayed in parallel with the structural abnormality degree map or may be superimposed and displayed. When both are superimposed, one of the front image and the structural abnormality degree map may be semi-transparent so that both can be visually recognizable at the same time.

The front image can be a variety of images. For example, the front image may be an OCT front image (as a particular example, an en-face image, a C-scan image, or the like) generated by using three-dimensional OCT data. Further, the front image may be the MC front image based on the motion contrast data. Further, it may be a front image captured by a fundus camera, an SLO, or the like. Note that, two or more of the plurality of types of front images may be simultaneously displayed or may be switched and displayed.

Further, the front image may be an image showing the distribution of the blood vessels. The image showing the distribution of the blood vessels may be, for example, the MC front image. Further, the image showing the distribution of the blood vessels may be a blood vessel density map showing the two-dimensional distribution of a blood vessel density. For example, even when the noise due to the blood vessels is depicted on the structural abnormality degree map, it is easy for the user to intuitively recognize that the noise is caused by the blood vessels via the MC front image displayed together. Further, the MC front image in the corresponding tissue may be displayed with respect to at least one of the two or more structural abnormality degree maps generated for each of the two or more tissues. As a result, it becomes easy to appropriately recognize whether or not the area having a high degree of abnormality is due to the blood vessels for each tissue. Further, the OCT front image for each tissue may be displayed in association with at least one of the structural abnormality degree maps in place of or additionally for the MC front image for each tissue. As a result, in the area where the degree of abnormality of the structure is high, it becomes easier for the user to preferably recognize whether or not the abnormality of the structure actually occurs.

Further, the front image may be an image quality map showing an image quality of the tomographic image at each position of the structural abnormality degree map. The image quality map may be, for example, an SSI map in which the signal strength for each A-scan is imaged. As described above, the worse the image quality, the larger the value of the degree of abnormality is likely to be. Therefore, by comparing the structural abnormality degree map with the image quality map, it becomes easier for the user to preferably recognize whether or not the area having a high degree of abnormality is caused by the low image quality.

Simultaneous Display of Analysis Image and Structural Abnormality Degree Map

Further, instead of or in addition to the front image, an analysis image graphically showing an analysis result with respect to the ophthalmic image (at least one of the tomographic image and the front image) may be simultaneously displayed with the structural abnormality degree map. The analysis image may show the analysis result related to the thickness of the tissue. The analysis image and the front image may be switched and displayed at the same position on the screen. The analysis image in the corresponding tissue may be displayed with respect to at least one of the two or more structural abnormality degree maps generated for each of the two or more tissues.

The analysis image may be an analysis map of either the tomographic image or the front image or may be an analysis chart. For example, a GCHART, a S/I chart, an ETDS chart, or the like may be utilized as the analysis chart showing the thickness of the tissue.

The structural abnormality degree map and the analysis image may be superimposed and displayed. For example, when a thickness map is superimposed as the analysis image, one of the degree of abnormality of the structure and the thickness is represented by a contour line, and the other thereof is represented by the gradation of the pixel so that the degree of abnormality of the structure and the thickness can be comprehensively checked, and the user can easily recognize the possibility of the abnormality accurately.

The plurality of structural abnormality degree maps described above may be displayed on a check screen. The check screen is displayed so that the user can check the captured tomographic image. At this time, of the plurality of tomographic images captured the same tissue of the subject eye, the controller may display the tomographic image having the highest degree of abnormality of the structure or the tomographic image having the degree of abnormality of the structure equal to or higher than a threshold value on the display device. For example, by displaying the tomographic image having a high degree of abnormality of the structure among the plurality of tomographic images on the check screen, the user can easily check the tomographic image obtained by imaging the site having a high degree of abnormality of the structure. Further, by displaying the tomographic image having a high degree of abnormality of the structure of the plurality of tomographic images when a viewer is activated to allow the user to check the captured tomographic image, the controller may first allow the user to check the tomographic image obtained by imaging the site having a high degree of abnormality of the structure.

The controller may execute processing of outputting an imaging instruction for imaging the site having the degree of abnormality of the structure equal to or higher than the threshold value on the structural abnormality degree map to the ophthalmic image capturing device. Further, the controller may execute processing of displaying the tomographic image or an enlarged image of the site having the degree of abnormality of the structure equal to or higher than the threshold value on the display device. In this case, the image of the site having a high degree of abnormality of the structure is appropriately checked by the user.

Note that, when the controller outputs the imaging instruction for imaging the site having the degree of abnormality of the structure equal to or higher than the threshold value, an instruction may be output to capture the tomographic image of the site having the degree of abnormality of the structure equal to or higher than the threshold value with higher image quality. For example, an instruction for acquiring a higher resolution tomographic image may be output. Further, an instruction may be output in which the tomographic image of the site having the degree of abnormality of the structure equal to or higher than the threshold value is captured a plurality of times and an average added image of the plurality of captured tomographic images is acquired. In this case, the tomographic image of the site having a high degree of abnormality of the structure is acquired with high image quality.

The controller may input the structural abnormality degree map into the mathematical model that outputs an automatic diagnosis result related to the disease of the subject eye. At this time, the type of disease may be output as the automatic diagnosis result. In this case, it is considered that the result focusing on the structural abnormality can be obtained and the automatic diagnosis result can be obtained efficiently, rather than searching or identifying the disease by using the tomographic image.

Example

Device Configuration

Hereinafter, one of the typical embodiments in the present disclosure will be described with reference to the drawings. As illustrated in FIG. 1, in the present embodiment, a mathematical model building device 1, an ophthalmic image processing device 21, and ophthalmic image capturing devices 11A and 11B are used. The mathematical model building device 1 builds a mathematical model by training the mathematical model using a machine learning algorithm. The built mathematical model outputs a probability distribution for identifying the tissue in the ophthalmic image based on the input ophthalmic image. The ophthalmic image processing device 21 acquires the probability distribution by using the mathematical model and acquires the degree of divergence between the acquired probability distribution and the probability distribution output in the case where the tissue is accurately identified as structural information indicating the degree of abnormality of the structure of the tissue. The ophthalmic image capturing devices 11A and 11B captures ophthalmic images which are images of a tissue of a subject eye.

As an example, a personal computer (hereinafter it is referred to as "PC") is used for the mathematical model building device 1 of the present embodiment. Details will be described later, a mathematical model building device 1 builds the mathematical model by training the mathematical model using the ophthalmic image (hereinafter it is referred to as "training ophthalmic image") acquired from the ophthalmic image capturing device 11A and training data indicating a position of at least one tissue in the training ophthalmic image. However, the device that can function as the mathematical model building device 1 is not limited to the PC. For example, the ophthalmic image capturing device 11A may function as the mathematical model building device 1. Further, controllers of a plurality of devices (for example, a CPU of the PC and a CPU 13A of the ophthalmic image capturing device 11A) may collaborate to build a mathematical model.

Further, a PC is used for the ophthalmic image processing device 21 of the present embodiment. However, the device that can function as the ophthalmic image processing device 21 is not limited to the PC. For example, the ophthalmic image capturing device 11B, a server, or the like may function as the ophthalmic image processing device 21. When the ophthalmic image capturing device (the OCT device in the present embodiment) 11B functions as the ophthalmic image processing device 21, the ophthalmic image capturing device 11B can acquire the degree of divergence from the captured ophthalmic image while capturing the ophthalmic image. Further, the ophthalmic image capturing device 11B can also image the appropriate site based on the acquired degree of divergence. Further, a mobile terminal such as a tablet terminal or a smartphone may function as the ophthalmic image processing device 21. Controllers of a plurality of devices (for example, a CPU of the PC and a CPU 13B of the ophthalmic image capturing device 11B) may collaborate to perform various processing.

Further, in the present embodiment, a case where a CPU is used as an example of a controller that performs various processing will be illustrated. However, it goes without saying that a controller other than the CPU may be used for at least a part of various devices. For example, by adopting a GPU as a controller, the processing speed may be increased.

The mathematical model building device 1 will be described. The mathematical model building device 1 is disposed, for example, in the ophthalmic image processing device 21 or a manufacturer that provides an ophthalmic image processing program to a user. The mathematical model building device 1 includes a controller 2 that performs various control processing and a communication I/F 5. The controller 2 includes a CPU 3 which is a controller that handles controls, and a storage device 4 capable of storing a program, data, and the like. The storage device 4 stores a mathematical model building program for executing mathematical model building processing (see FIG. 2) described later. Further, the communication I/F 5 connects the mathematical model building device 1 to other devices (for example, the ophthalmic image capturing device 11A and the ophthalmic image processing device 21).

The mathematical model building device 1 is connected to an operation unit 7 and a display device 8. The operation unit 7 is operated by the user in order for the user to input various instructions to the mathematical model building device 1. For the operation unit 7, for example, at least one of a keyboard, a mouse, a touch panel, and the like can be used. Note that a microphone or the like for inputting various instructions may be used together with the operation unit 7 or instead of the operation unit 7. The display device 8 displays various images. As the display device 8, various devices capable of displaying an image (for example, at least one of a display device, a display, a projector, or the like) can be used. Note that the "image" in the present disclosure includes both a still image and a moving image.

The mathematical model building device 1 can acquire ophthalmic image data (hereinafter, it may be simply referred to as an "ophthalmic image") from the ophthalmic image capturing device HA. The mathematical model building device 1 may acquire the ophthalmic image data from the ophthalmic image capturing device 11A by, for example, at least one of wired communication, wireless communication, an attachable and detachable storage medium (for example, a USB memory), and the like.

Figure 5:
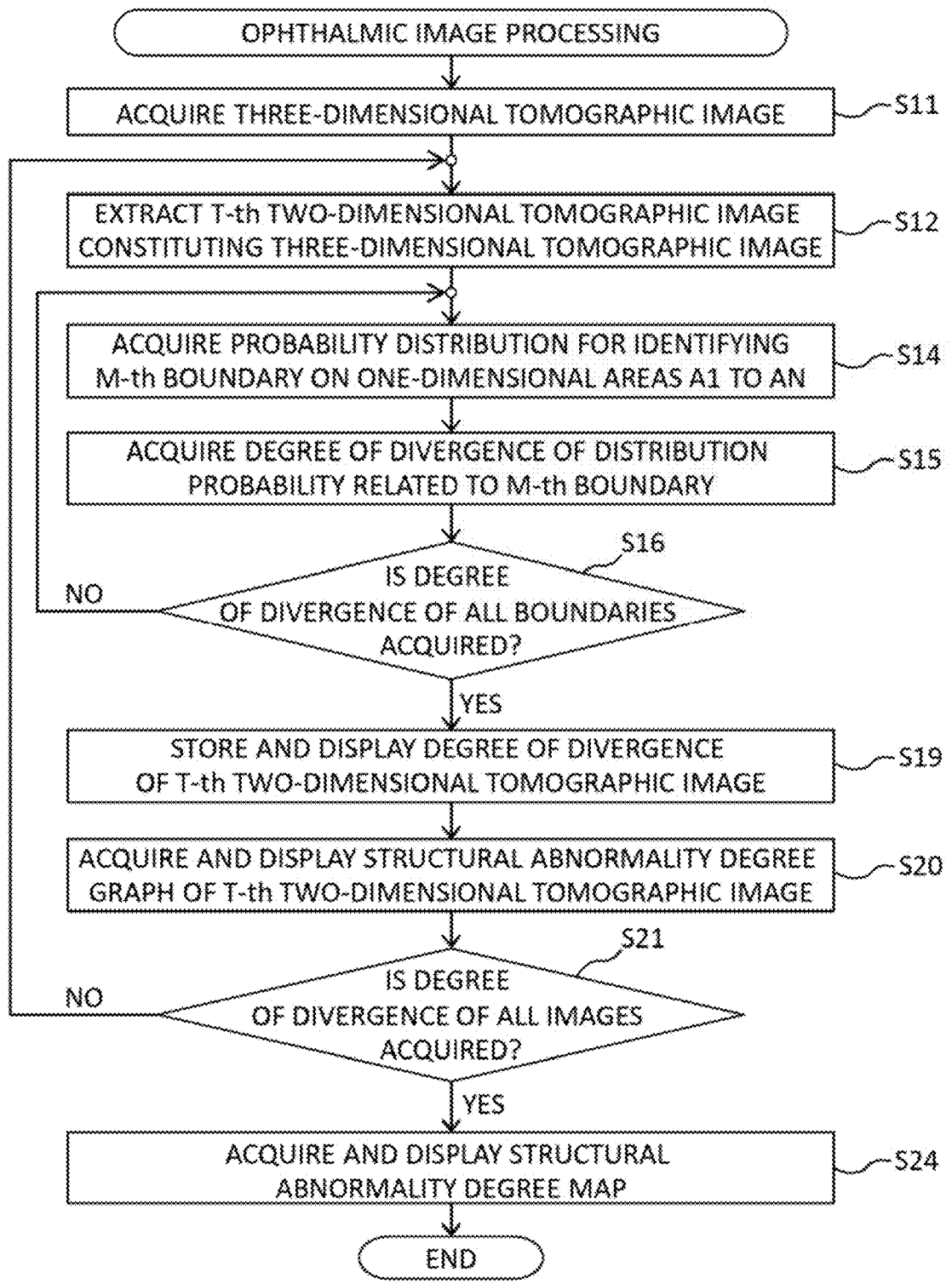
FIG. 5 is a flowchart of ophthalmic image processing executed by the ophthalmic image processing device 21.

The ophthalmic image processing device 21 will be described. The ophthalmic image processing device 21 is disposed, for example, in a facility (for example, a hospital, a health examination facility, or the like) that performs diagnosis, examination, or the like of a person to be examined. The ophthalmic image processing device 21 includes a controller 22 that performs various control processing and a communication I/F 25. The controller 22 includes a CPU 23 which is a controller that handles controls, and a storage device 24 capable of storing a program, data, and the like. The storage device 24 stores an ophthalmic image processing program for executing ophthalmic image processing (see FIG. 5) described later. The ophthalmic image processing program includes a program that realizes a mathematical model built by the mathematical model building device 1. The communication I/F 25 connects the ophthalmic image processing device 21 to other devices (for example, the ophthalmic image capturing device 11B and the mathematical model building device 1).

The ophthalmic image processing device 21 is connected to the operation unit 27 and the display device 28. Various devices can be used for the operation unit 27 and the display device 28 in the same manner as the operation unit 7 and the display device 8 described above.

The ophthalmic image processing device 21 can acquire the ophthalmic image from the ophthalmic image capturing device 11B. The ophthalmic image processing device 21 may acquire the ophthalmic image from the ophthalmic image capturing device 11B by, for example, at least one of wired communication, wireless communication, an attachable and detachable storage medium (for example, a USB memory), and the like. Further, the ophthalmic image processing device 21 may acquire a program or the like for realizing the mathematical model built by the mathematical model building device 1 via communication or the like.

The ophthalmic image capturing devices 11A and 11B will be described. As an example, in the present embodiment, a case where the ophthalmic image capturing device 11A for providing the ophthalmic image to the mathematical model building device 1 and the ophthalmic image capturing device 11B for providing the ophthalmic image to the ophthalmic image processing device 21 are used, will be described. However, the number of ophthalmic image capturing devices used is not limited to two. For example, the mathematical model building device 1 and the ophthalmic image processing device 21 may acquire ophthalmic images from a plurality of ophthalmic image capturing devices. Further, the mathematical model building device 1 and the ophthalmic image processing device 21 may acquire the ophthalmic image from one common ophthalmic image capturing device. Note that the two ophthalmic image capturing devices 11A and 11B illustrated in the present embodiment have the same configuration. Therefore, the two ophthalmic image capturing devices 11A and 11B will be collectively described below.

Further, in the present embodiment, the OCT device is exemplified as the ophthalmic image capturing device 11 (11A, 11B).

The ophthalmic image capturing device 11 (11A, 11B) includes a controller 12 (12A, 12B) that performs various control processing, and an ophthalmic image capturing unit 16 (16A, 16B). The controller 12 includes a CPU 13 (13A, 13B) which is a controller that handles controls, and a storage device 14 (14A, 14B) capable of storing a program, data, and the like.

The ophthalmic image capturing unit 16 includes various configurations necessary for capturing an ophthalmic image of a subject eye. The ophthalmic image capturing unit 16 of the present embodiment is provided with an OCT light source, a branched optical element that branches OCT light emitted from the OCT light source into measurement light and reference light, a scanning unit for scanning the measurement light, an optical system for irradiating a subject eye with the measurement light, a light receiving element for receiving combined light of the light reflected by the tissue of the subject eye and the reference light, and the like.

The ophthalmic image capturing device 11 can capture a two-dimensional tomographic image and a three-dimensional tomographic image of the fundus of the subject eye. Specifically, the CPU 13 captures the two-dimensional tomographic image of a cross section intersecting a scan line by scanning the OCT light (measurement light) on the scan line. The two-dimensional tomographic image may be an average added image generated by performing the average added processing with respect to the plurality of tomographic images of the same site. Further, the CPU 13 can capture a three-dimensional tomographic image of the tissue by scanning the OCT light two-dimensionally. For example, the CPU 13 acquires a plurality of two-dimensional tomographic images by scanning each of a plurality of scan lines having different positions with the measurement light in a two-dimensional area when the tissue is viewed from the front. Next, the CPU 13 acquires the three-dimensional tomographic image by combining the plurality of captured two-dimensional tomographic images.

Mathematical Model Building Processing

Figure 3:
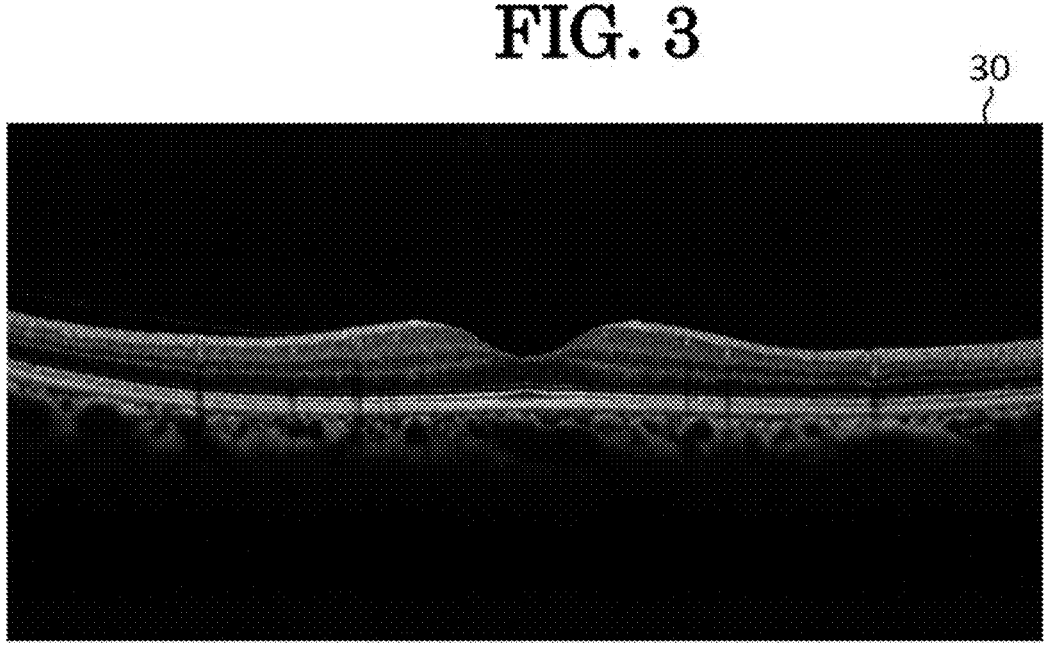
FIG. 3 is a diagram illustrating an example of a training ophthalmic image 30.
Figure 4:
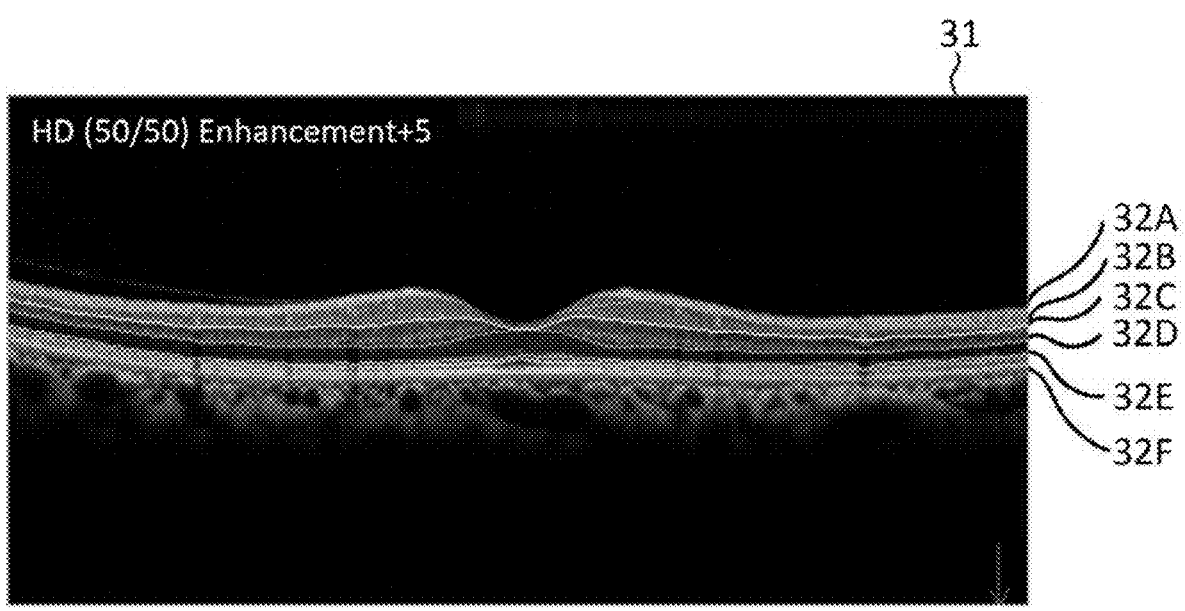
FIG. 4 is a diagram illustrating an example of training data 31.

The mathematical model building processing that is executed by the mathematical model building device 1 will be described with reference to FIGS. 2 to 4. The mathematical model building processing is executed by the CPU 3 according to the mathematical model building program stored in the storage device 4. In the mathematical model building processing, the mathematical model that outputs the probability distribution for identifying the tissue in the ophthalmic image is built by training the mathematical model by using the training data set. The training data set includes input side data (input training data) and output side data (output training data).

Figure 2:
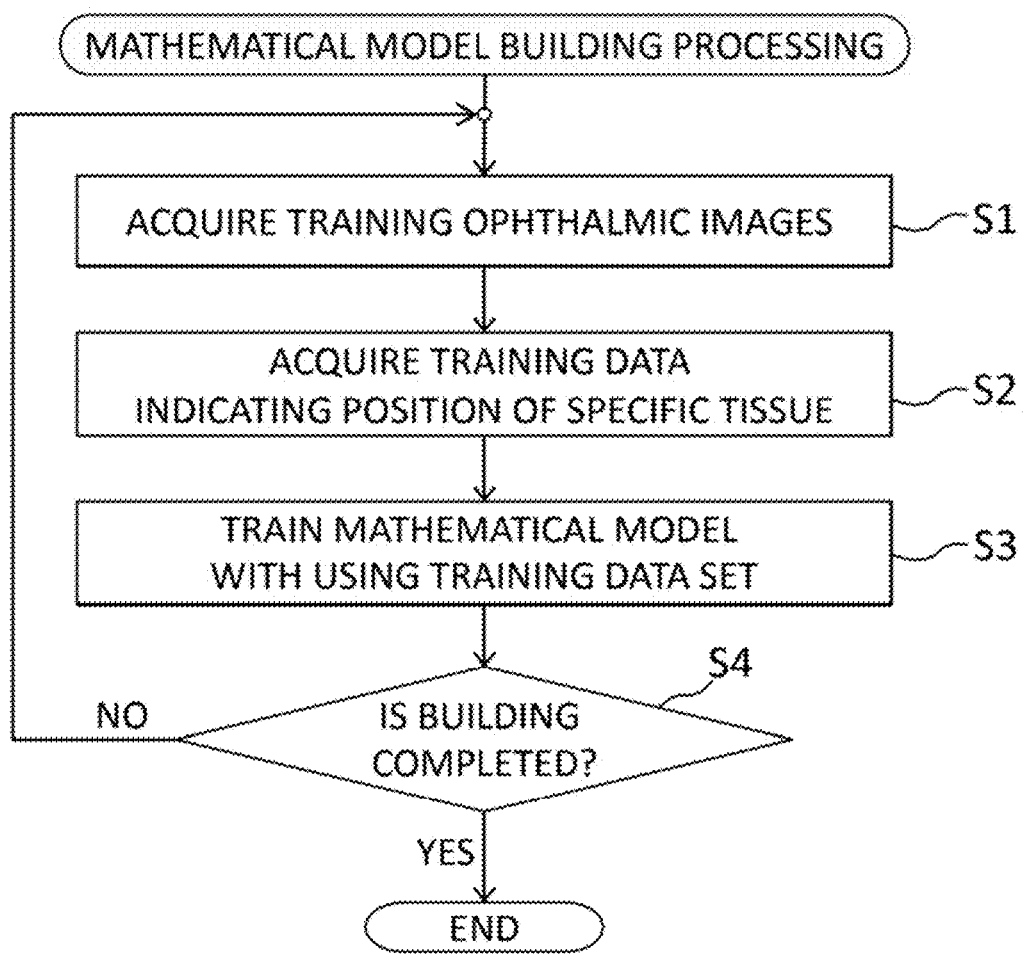
FIG. 2 is a flowchart of mathematical model building processing executed by the mathematical model building device 1.

As illustrated in FIG. 2, the CPU 3 acquires the data of the training ophthalmic image, which is the ophthalmic image captured by the ophthalmic image capturing device 11A, as the input training data (S1). In the present embodiment, the data of the training ophthalmic image is generated by the ophthalmic image capturing device 11A and then acquired by the mathematical model building device 1. However, the CPU 3 may acquire a signal (for example, an OCT signal) that is a basis for generating the training ophthalmic image from the ophthalmic image capturing device 11A and acquire the data of the training ophthalmic image by generating the training ophthalmic image based on the acquired signal.

Note that, in S1 of the present embodiment, the two-dimensional tomographic image captured by the ophthalmic image capturing device 11A, which is an OCT device, is acquired as the training ophthalmic image. FIG. 3 illustrates an example of the training ophthalmic image 30 which is the two-dimensional tomographic image of the fundus. The training ophthalmic image 30 illustrated in FIG. 3 represents a plurality of layers in the fundus. Note that, in the present embodiment, the training ophthalmic images included in the training data set may be the ophthalmic images of the tissues having a low degree of abnormality of the structure but are not necessarily limited to these. For example, the ophthalmic images having a high degree of abnormality of the structure for a part of tissues may be included in the training data set. Even in a diseased eye, the tissue is not formed only by abnormal structures but includes many normal structures. Therefore, even when the ophthalmic images having a high degree of abnormality of the structure for a part of tissues are present in the training data set, in the training data set, the data for the normal structures is likely to be sufficiently larger than the data for the abnormal structures, so it is unlikely that a tissue identification using the mathematical model is not adversely affected. Further, it is possible to consider that the accuracy of the identification can be improved by the appropriate presence of data for the abnormal structures in the training data set.

Next, of the tissues in the training ophthalmic image, the CPU 3 acquires the training data indicating the position of at least one of the tissues (S2). FIG. 4 illustrates an example of the training data 31 when the two-dimensional tomographic image of the fundus is used as the training ophthalmic image 30. Of the plurality of tissues shown in the training ophthalmic image 30 (specifically, a plurality of layers and boundaries), data of labels 32A to 32F indicating the positions of each of the six boundaries are included in the training data 31 illustrated in FIG. 4. In the present embodiment, the data of the labels 32A to 32F in the training data 31 is generated by a worker operating the operation unit 7 while looking at the boundary in the training ophthalmic image 30. However, it is also possible to change the method of generating data of labels.

Note that, it is also possible to change the training data. For example, when the two-dimensional tomographic image of the fundus is used as the training ophthalmic image 30, the training data may be data indicating the position of at least one layer in the fundus. Further, the training data may be data indicating the position of a spot-shaped site and the like in the tissue instead of the layer and boundary.

Next, the CPU 3 uses the training data set and executes training of the mathematical model by using a machine learning algorithm (S3). As the machine learning algorithm, for example, a neural network, a random forest, a boosting, a support vector machine (SVM), and the like are generally known.

The neural network is a technique that mimics the behavior of biological nerve cell networks. The neural network includes, for example, a feed-forward (forward propagation) neural network, an RBF network (radial basis function), a spiking neural network, a convolutional neural network, a recursive neural network (a recurrent neural network, a feedback neural network, or the like), a stochastic neural network (a Boltzmann machine, a Basian network, or the like), or the like.

The random forest is a method of performing learning based on randomly sampled training data to generate a large number of decision trees. When using the random forest, branches of a plurality of decision trees that are trained in advance as an identifier are traced, and the average (or majority vote) of the results obtained from each decision tree is taken.

The boosting is a method of generating a strong identifier by combining a plurality of weak identifiers. A strong identifier is built by sequentially made a simple and weak identifier to learn.

The SVM is a method of configuring two classes of pattern identifiers by using linear input elements. By using the training data, the SVM learns the parameters of the linear input element based on, for example, the criterion (hyperplane separation theorem) of obtaining the margin maximizing hyperplane that maximizes the distance from each data point.

The mathematical model refers, for example, to a data structure for predicting a relationship between the input data and the output data. The mathematical model is built by being trained with the training data set. As described above, the training data set is a set of input training data and output training data. For example, correlation data of each input and output (for example, weights) is updated by training.

In the present embodiment, a multi-layer neural network is used as a machine learning algorithm. The neural network includes an input layer for inputting data, an output layer for generating data to be predicted, and one or more hidden layers between the input layer and the output layer. A plurality of nodes (also called units) are disposed in each layer. Specifically, in the present embodiment, a convolutional neural network (CNN), which is a kind of multi-layer neural network, is used.

As an example, the mathematical model built in the present embodiment outputs the probability distribution, which uses the coordinates (either one of the one-dimensional coordinates, two-dimensional coordinates, three-dimensional coordinates, and four-dimensional coordinates) where the specific tissue (for example, a specific boundary, a specific layer, a specific site, or the like) exists as a probability variable in the area (either one of the one-dimensional area, two-dimensional area, three-dimensional area, and four-dimensional area that includes the time axis) in the ophthalmic image, as a probability distribution for identifying the tissue. In the present embodiment, a softmax function is applied in order to have the mathematical model output the probability distribution. Specifically, the mathematical model built in S3 outputs the probability distribution having the coordinates where the specific boundary exists in the one-dimensional area extending in the direction (in the present embodiment, it is the A-scan direction of OCT) intersecting the specific boundary in the two-dimensional tomographic image, as a probability variable.

However, the specific method for outputting the probability distribution for the mathematical model to identify the tissue can be changed as appropriate. For example, in the two-dimensional area or three-dimensional area, the mathematical model may output the probability distribution, which uses the two-dimensional coordinates or three-dimensional coordinates where the specific tissue (for example, the characteristic site) exists as a probability variable, as a probability distribution for identifying the tissue. Further, the mathematical model may output the probability distribution having the type of a plurality of tissues (for example, a plurality of layers and boundaries) in the subject eye as a probability variable, for each area (for example, for each pixel) of the input ophthalmic image. Further, the ophthalmic image input into the mathematical model may be a moving image.

Further, other machine learning algorithms may be used. For example, a hostile generative network (Generative adversarial networks: GAN) that utilizes two competing neural networks may be adopted as a machine learning algorithm.

The processes S1 to S3 are repeated until the building of the mathematical model is completed (S4: NO). When the building of the mathematical model is completed (S4: YES), the mathematical model building processing ends. The program and data for realizing the built mathematical model are incorporated in the ophthalmic image processing device 21.

Ophthalmic Image Processing

Ophthalmic image processing executed by the ophthalmic image processing device 21 will be described with reference to FIGS. 5 to 11. The ophthalmic image processing is executed by the CPU 23 according to the ophthalmic image processing program stored in the storage device 24.

First, the CPU 23 acquires the three-dimensional tomographic image of the tissue of the subject eye (the fundus in the present embodiment) (S11). The three-dimensional tomographic image is captured by the ophthalmic image capturing device 11B and acquired by the ophthalmic image processing device 21. As described above, the three-dimensional tomographic image is composed by combining a plurality of two-dimensional tomographic images captured by scanning on different scan lines with the measurement light. Note that the CPU 23 may acquire a signal (for example, an OCT signal) that is a basis for generating a three-dimensional tomographic image from the ophthalmic image capturing device 11B and generate the three-dimensional tomographic image based on the acquired signal.

Figure 6:
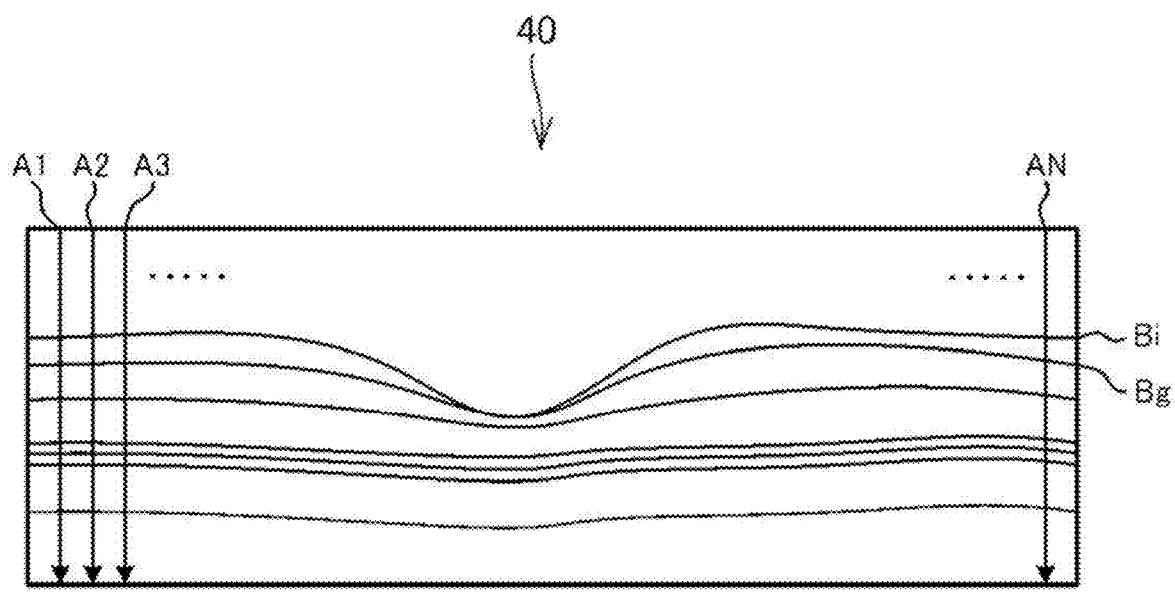
FIG. 6 is a diagram schematically illustrating a relationship between a two-dimensional tomographic image 40 input into a mathematical model and one-dimensional areas A1 to AN in the two-dimensional tomographic image 40.

The CPU 23 extracts the T-th (an initial value of T is "1") two-dimensional tomographic image from the plurality of two-dimensional tomographic images constituting the acquired three-dimensional tomographic image (S12). FIG. 6 illustrates an example of the two-dimensional tomographic image 40. The two-dimensional tomographic image 40 represents a plurality of boundaries in the fundus of the subject eye. In the example illustrated in FIG. 6, a plurality of boundaries including a boundary Bi, which is an inner limiting membrane (ILM), and a boundary Bg between a nerve fiber layer (NFL) and a ganglion cell layer (GCL) appear. Further, a plurality of one-dimensional areas A1 to AN are set in the two-dimensional tomographic image 40. In the present embodiment, the one-dimensional areas A1 to AN set in the two-dimensional tomographic image 40 extend along an axis that intersects the specific boundary (in the present embodiment, the plurality of boundaries including the boundary Bi and boundary Bg). Specifically, the one-dimensional areas A1 to AN of the present embodiment match each area of a plurality of (N) A-scans constituting the two-dimensional tomographic image 40 captured by the OCT device.

Note that it is also possible to change the method of setting the plurality of one-dimensional areas. For example, the CPU 23 may set the plurality of one-dimensional areas so that the angle between the axis of each one-dimensional area and the specific boundary is as close to vertical as possible. In this case, the position and angle of each one-dimensional area may be set so that the angle approaches vertically, for example, based on the shape of a general tissue of the subject eye (the fundus in the present embodiment).

Figure 7:
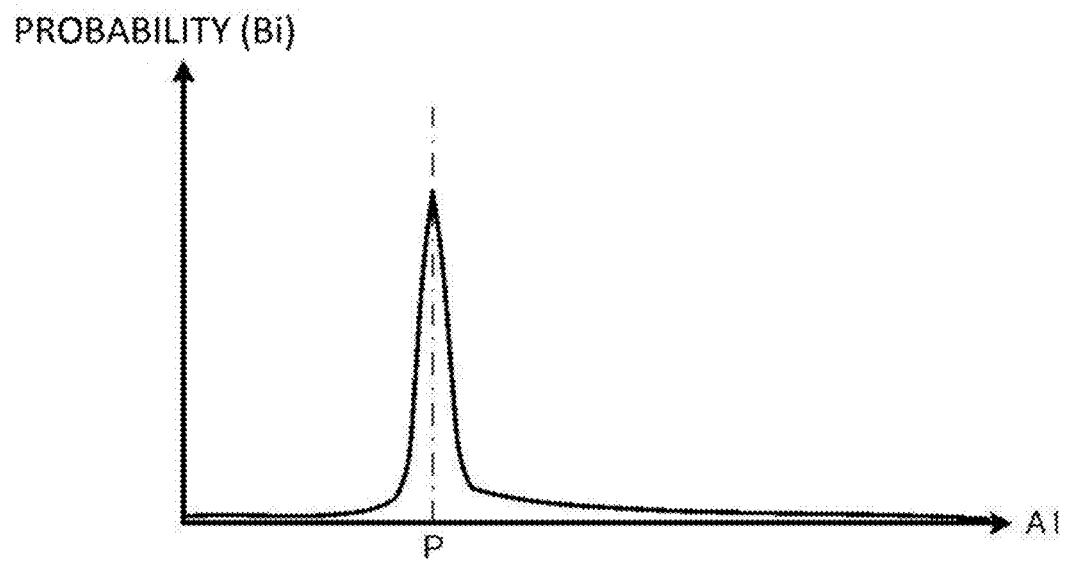
FIG. 7 is an example of a graph illustrating a probability distribution for identifying a boundary Bi when a degree of abnormality of a structure in the vicinity of the boundary Bi is low.
Figure 8:
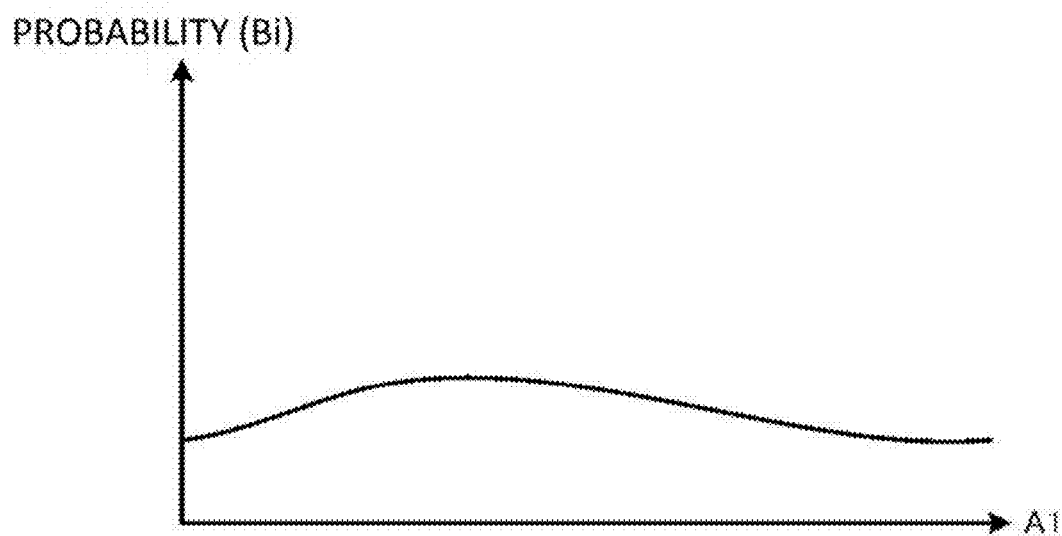
FIG. 8 is an example of a graph illustrating a probability distribution for identifying the boundary Bi when the degree of abnormality of the structure in the vicinity of the boundary Bi is high.

By inputting the T-th two-dimensional tomographic image into the mathematical model, the CPU 23 acquires the probability distribution of the coordinates where the M-th boundary (an initial value of M is "1") exists in each of the plurality of one-dimensional areas A1 to AN, as a probability distribution for identifying the tissue (S14). FIGS. 7 and 8 illustrate an example of a graph showing the probability distribution of the coordinates where the boundary Bi exists, which is acquired from the one-dimensional coordinates A1. In the example illustrated in FIGS. 7 and 8, the probability distribution of the coordinates where the boundary Bi exists is illustrated, using the one-dimensional coordinates of the one-dimensional area A1 as a probability variable. That is, in the example illustrated in FIGS. 7 and 8, the horizontal axis is a probability variable, the vertical axis is the probability of the probability variable, and the probability variable is the coordinates where the boundary Bi exists in the one-dimensional area A1. In S14, the probability distributions in each of the plurality of one-dimensional areas A1 to AN are acquired.

The probability distribution illustrated in FIG. 7 is an example of the probability distribution output when the degree of abnormality of the structure of the tissue (specifically, the tissue in the vicinity of the boundary Bi) is low. At a position where the degree of abnormality of the structure is low, the tissue is easily identified accurately by using the mathematical model, so the probability of the position of the tissue tends to be biased. According to the graph illustrated in FIG. 7, among each of the points on the one-dimensional area A1, the point at which the boundary Bi is most likely to exist can be determined to be the point P. The probability distribution (that is, the ideal probability distribution) when the mathematical model accurately identifies the tissue takes a value of 1 at only one point on the one-dimensional area A1 and is 0 at the other points.

On the other hand, the probability distribution illustrated in FIG. 8 is an example of the probability distribution output when the degree of abnormality of the structure of the tissue is high. As illustrated in FIG. 8, the probability distribution is less likely to be biased at a position where the degree of abnormality of the structure is high. As described above, the bias of the probability distribution for identifying the tissue changes according to the degree of abnormality of the structure of the tissue.

Next, the CPU 23 acquires the degree of divergence of the probability distribution P related to the M-th boundary (S15). The degree of divergence is a difference of the probability distribution P acquired in S14 with respect to the probability distribution output in the case where the tissue is accurately identified. In the present embodiment, the degree of divergence is acquired as the structural information indicating the degree of abnormality of the structure of the tissue. In S15 of the present embodiment, the degree of divergence is acquired (calculated) for each of the plurality of probability distributions P acquired for the plurality of one-dimensional areas A1 to AN.

In the present embodiment, the entropy of the probability distribution P is calculated as the degree of divergence. The entropy is given by the following Equation 2. The entropy H(P) takes a value of 0≤H(P)≤log(number of events) and becomes a smaller value as the probability distribution P is biased. That is, the smaller the entropy H(P), the lower the degree of abnormality of the structure of the tissue. The entropy of the probability distribution output in the case where the tissue is accurately identified is 0. Further, the entropy H(P) increases as the degree of abnormality of the structure of the tissue increases and it becomes difficult to identify the tissue. Therefore, by using the entropy H(P) of the probability distribution P as the degree of divergence, the degree of abnormality of the structure of the tissue is appropriately quantified.

$$H(P) = -\sum p \log(p) \quad \text{(Equation 2)}$$

However, a value other than entropy may be adopted as the degree of divergence. For example, at least one of the standard deviation, the coefficient of variation, the variance, and the like indicating the degree of dispersion of the acquired probability distribution P may be used as the degree of divergence. The KL divergence or the like, which is a measure for measuring the difference between probability distributions P, may be used as the degree of divergence. Further, the maximum value of the acquired probability distribution P (for example, the maximum value of the probabilities illustrated in FIGS. 7 and 8) may be used as the degree of divergence. Further, the difference between the maximum value of the acquired probability distribution P and the second largest value may be used as the degree of divergence.

Next, the CPU 23 determines whether or not the degree of divergence of all the boundaries to be detected in the T-th two-dimensional tomographic image is acquired (S16). When the degree of divergence of a part of the boundary is not acquired (S16: NO), "1" is added to the order M of the boundary (S17), the process returns to S14, and the degree of divergence of the next boundary is acquired (S14, S15). When the degree of divergence of all the boundaries is acquired (S16: YES), the CPU 23 stores the degree of divergence of the T-th two-dimensional tomographic image in the storage device 24 and displays the degree of divergence on the display device 28 (S19). The CPU 23 acquires (generates in the present embodiment) a structural abnormality degree graph of the T-th two-dimensional tomographic image and displays the graph on the display device 28 (S20).

Figure 9:
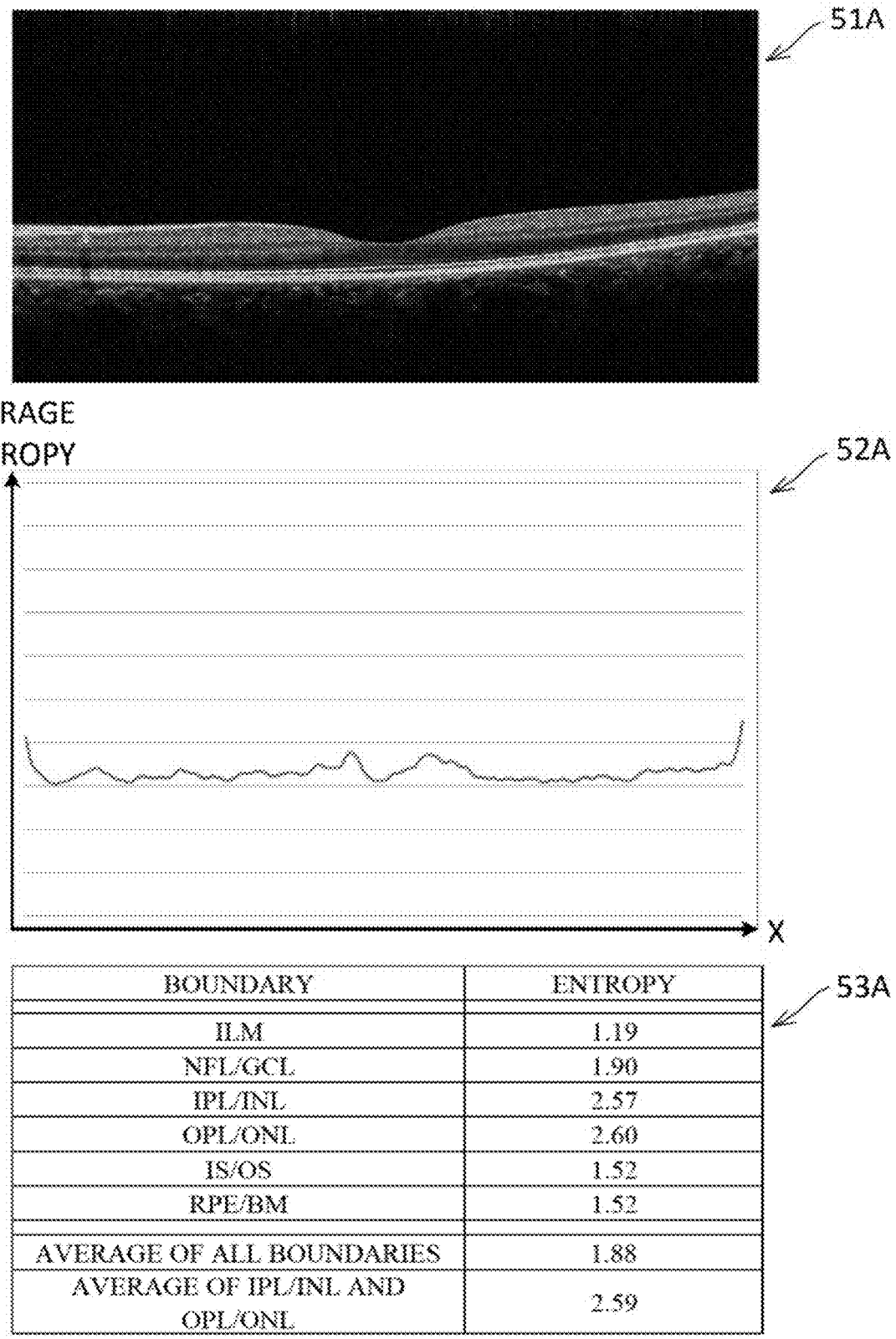
FIG. 9 is an example of a display screen on which a two-dimensional tomographic image 51A, a structural abnormality degree graph 52A, and a degree of divergence table 53A are displayed.

The structural abnormality degree graph 52 will be described with reference to FIGS. 9 and 10. FIG. 9 illustrates an example of a display screen on which a two-dimensional tomographic image 51A having a low degree of abnormality of the structure, a structural abnormality degree graph 52A related to the two-dimensional tomographic image 51A, and a degree of divergence table 53A showing the degree of divergence related to the two-dimensional tomographic image 51A are displayed. Further, FIG. 10 illustrates an example of a display screen on which a two-dimensional tomographic image 51B having a high degree of abnormality of the structure, a structural abnormality degree graph 52B related to the two-dimensional tomographic image 51B, and a degree of divergence table 53B showing the degree of divergence related to the two-dimensional tomographic image 51B are displayed.

Figure 10:
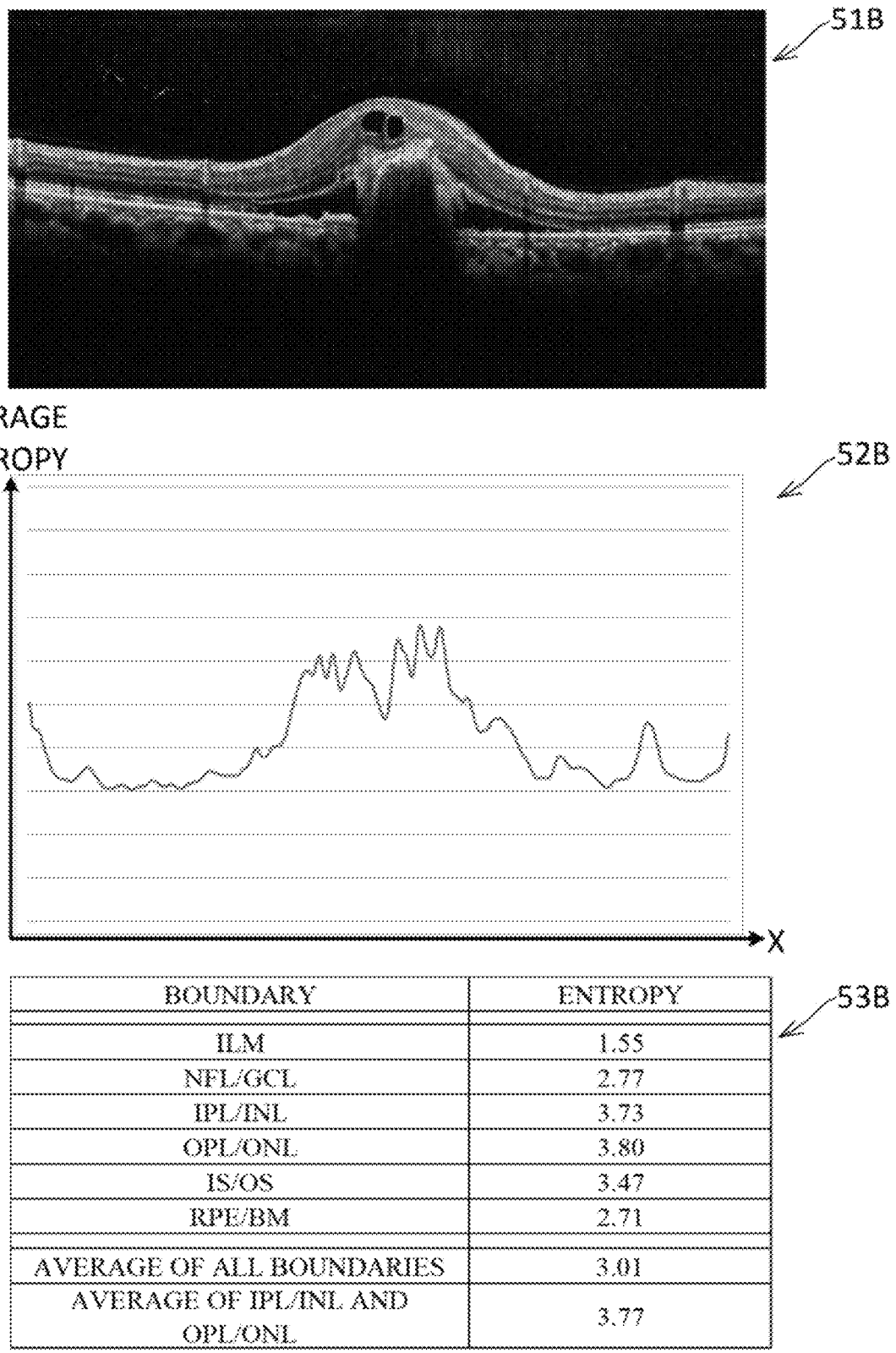
FIG. 10 is an example of a display screen on which a two-dimensional tomographic image 51B, a structural abnormality degree graph 52B, and a degree of divergence table 53B are displayed.

As illustrated in FIGS. 9 and 10, the two-dimensional tomographic image 51 is a two-dimensional image spreading in the X direction (horizontal direction of the drawing) and the Z direction (vertical direction of the drawing). As described above, the degree of divergence is acquired for each of a plurality of axes extending parallel to the Z direction on the ophthalmic image (in the present embodiment, the plurality of A-scans). In the structural abnormality degree graph 52 illustrated in FIGS. 9 and 10, the horizontal axis is the X axis, and the degree of divergence at each of the positions in the X direction is shown on the vertical axis.

As an example, in the structural abnormality degree graph 52 of the present embodiment, the average value of the plurality of degrees of divergence (the entropy in the present embodiment) acquired for each of the plurality of boundaries is shown for each position in the X direction. However, the degree of divergence of one boundary may be shown with the structural abnormality degree graph 52. Further, the average value of the plurality of specific boundaries (for example, the boundary of IPL/INL and the boundary of OPL/ONL) may be shown with the structural abnormality degree graph 52. Further, instead of the average value, various statistical values other than the average value (for example, a median value, a mode value, the maximum value, the minimum value, or the like) may be used.

As illustrated in FIG. 9, when the degree of abnormality of the structure is low in the entire X direction, the degree of divergence shown with the structural abnormality degree graph 52A becomes a low value in the entire X direction. On the other hand, as illustrated in FIG. 10, at the position in the X direction where the degree of abnormality of the structure is high, the degree of divergence shown with the structural abnormality degree graph 52B becomes a high value. As described above, according to the structural abnormality degree graph 52, the user can appropriately recognize which position in the X direction has a high degree of abnormality.

An example of a method of displaying the degree of divergence will be described with reference to FIGS. 9 and 10. As shown in FIGS. 9 and 10, in the degree of divergence table 53 of the present embodiment, the acquired degree of divergence (the entropy in the present embodiment) is displayed for each of the plurality of boundaries. Therefore, the user can appropriately recognize the boundary having a high degree of abnormality of the structure based on the quantified value. The degree of divergence displayed in the degree of divergence table 53 of the present embodiment is the average value of the plurality of degrees of divergence acquired for each of the plurality of one-dimensional areas (the A-scan in the present embodiment). Further, in the degree of divergence table 53 of the present embodiment, the average value of the degree of divergence related to all the boundaries is displayed. Therefore, the user can easily recognize from the average value whether or not there is a site having a high degree of abnormality of the structure in the tissue shown in the ophthalmic image. Further, in the degree of divergence table 53 of the present embodiment, the average value of the degree of divergence related to the plurality of specific boundaries of all the boundaries is displayed. As an example, in the present embodiment, the average value of the boundaries (the IPL/INL boundary and the OPL/ONL boundary) in which the structure tends to collapse due to the influence of the disease is displayed. Therefore, the user can easily recognize whether or not there is a structural abnormality due to the disease. Note that as described above, various statistical values other than the average value may be used.

Next, the CPU 23 determines whether or not the degree of divergence of all the two-dimensional tomographic images constituting the three-dimensional tomographic image is acquired (S21). When the degree of divergence of a part of the two-dimensional tomographic images is not acquired (S21: NO), "1" is added to the order T of the two-dimensional tomographic images (S22), the process returns to S12, and the degree of divergence of the next two-dimensional tomographic image is acquired (S12 to S20). When the degree of divergence of all the two-dimensional tomographic images is acquired (S21: YES), the CPU 23 acquires (generates in the present embodiment) the structural abnormality degree map and displays the map on the display device 28 (S24).

The structural abnormality degree map will be described with reference to FIG. 11. The structural abnormality degree map shows the two-dimensional distribution of the degree of divergence in the tissue. The structural abnormality degree map of the present example shows the two-dimensional distribution of the degree of divergence when the tissue (the fundus in the present embodiment) is viewed from the front. However, the direction indicating the two-dimensional distribution may be changed as appropriate. Further, the degree of divergence is acquired for each of the plurality of two-dimensional tomographic images constituting the three-dimensional tomographic image, and then the degree of divergence of the entire tissue is acquired. The degree of divergence of the entire tissue referred to here can be rephrased as the degree of divergence at first to sixth layer boundaries corresponding to the labels 32A to 32F (see FIG. 4) in the present example.

In the present example, as an example, the structural abnormality degree maps 51A to 51F of the first to sixth layer boundaries corresponding to each of the labels 32A to 32F (see FIG. 4) are generated based on the degree of divergence of each of the layer boundaries. FIG. 11 illustrates an example of the display mode of the structural abnormality degree maps 51A to 51F in the display device 28.

The structural abnormality degree maps 51A to 51F may be graphs representing the degree of divergence at each position as a color or a shade. At this time, the gradation value of each pixel in the structural abnormality degree maps 51A to 51F is converted from the degree of divergence at each position of the layer boundary. For example, in the structural abnormality degree maps 51A to 51F illustrated in FIG. 11, the degree of divergence is shown in the gray scale. In the present example, the degree of divergence (entropy in the present example) is calculated in a range of 0 to 1, so that each value in the range of 0 to 1 is converted into, for example, the gradation value of 0 to 255 and represented on the map. In the structural abnormality degree maps 51A to 51F illustrated in FIG. 11, the pixel with the higher degree of divergence is represented as the smaller gradation value (that is, the higher luminance). Note that, the correspondence relationship between the degree of divergence and the gradation value is the same between the structural abnormality degree maps 51A to 51F illustrated in FIG. 11. However, the specific method for showing the degree of divergence of each position in the structural abnormality degree map is not limited to the gray scale and can be appropriately changed such as a color map or a three-dimensional map.

The structural abnormality degree maps 51A to 51F illustrated as an example in FIG. 11 are the processing results with respect to the subject eye having peeling on the deep layer side. From the structural abnormality degree maps 51A to 51F, it is seen that areas having a high degree of divergence at the center of the plurality of maps are represented in the plurality of structural abnormality degree maps 51B to 51F at least from the second layer boundary to the sixth layer boundary. Therefore, the user can easily recognize that there is a possibility of an abnormality of the structure affecting the plurality of layers based on the plurality of structural abnormality degree maps 51A to 51F. Further, as another example, of the plurality of structural abnormality degree maps generated for each layer boundary, when only a small number of maps represent areas having a high degree of divergence, the user can be recognized of the possibility of a more local abnormality of the structure as compared with the example. As described above, the display of the plurality of structural abnormality degree maps is useful for the user to quickly recognize the whole picture of the structural abnormality.

As illustrated in FIG. 11, in the present example, the front image 52 of the fundus is displayed simultaneously with the structural abnormality degree maps 51A to 51F. In the present example, an imaging range of the front image 52 corresponds to the structural abnormality degree maps 51A to 51F. By comparing with the front image 52, the user can check where on the structural abnormality degree maps 51A to 51F having a high degree of divergence is present on the fundus. The front image 52 in the present example may be, for example, an OCT front image. At this time, the front image 52 may be an MC front image which is a kind of OCT front image. The blood vessels are depicted in the MC front image. Therefore, for example, it is easy for the user to recognize whether or not the area having a high degree of abnormality is derived from the blood vessel on the structural abnormality degree maps 51A to 51F.

Further, when the OCT front image is displayed as the front image 52, the OCT front image related to any boundary may be displayed as the front image 52. At this time, the OCT front image for each boundary may be selectable in response to the user's operation. For example, by inputting a selection operation for any of the structural abnormality degree maps 51A to 51F, the OCT front image related to the boundary corresponding to the selected map may be displayed as the front image 52. By simultaneously displaying the desired structural abnormality degree map and the OCT front image of the corresponding layer, it is easy for the user to recognize the presence or absence of an abnormality at a position having a high degree of divergence in the structural abnormality degree map.

Further, in the present example, the correspondence relationship between the degree of divergence and the gradation value in each of the structural abnormality degree maps 51A to 51F can be individually changeable for each map. In FIG. 11, sliders 53A to 53F are installed adjacent to each of the structural abnormality degree maps 51A to 51F as examples of a GUI widget for changing the correspondence relationship between the degree of divergence and the gradation value. In each of the sliders 53A to 53F, positions of knob can be changed based on individual operations. In each of the structural abnormality degree maps 51A to 51F, the gamma value when converting the degree of divergence into the gradation value is changed according to the position of knob. In the present example, the gamma value decreases as the position of knob is moved to the left, and the gamma value increases as the position of knob is moved to the right. By operating the sliders 53A to 53F, the sensitivity of the structural abnormality degree maps 51A to 51F can be changed afterward.

That is, as the gamma value decreases, the map becomes a low-sensitivity map in which the position of a higher degree of divergence is highlighted on the map. On the contrary, as the gamma value increases, the map becomes more sensitive, and a subtle abnormality of the structure can be made conspicuous on the map. Note that, an initial position of knob (that is, an initial value of the gamma value) may be constant or may be determined based on the noise level of the two-dimensional tomographic image constituting the three-dimensional tomographic image.

For example, in the fundus of the eye, the fovea, the optic disc, and the blood vessels are present, which are tissues originally tend to have a high degree of divergence (hereinafter referred to as a specific tissue). The influence of the specific tissue is conspicuously depicted in some of the structural abnormality degree maps 51A to 51F of the first to sixth layer boundaries illustrated in FIG. 11. The depiction based on the specific tissue may become noise in recognizing the abnormality from the structural abnormality degree maps 51A to 51F. In such a case, in a map where the depiction based on the specific tissue is conspicuous, by decreasing the gamma value and lowering the sensitivity, it may be possible to clarify the position of possible abnormality while bringing the depiction based on the specific tissue closer to a background side. Further, for example, as in the structural abnormality degree map 51A of the first layer boundary illustrated in FIG. 11, when a conspicuous abnormal site is not seen, by increasing the gamma value to increase the sensitivity, the subtle abnormality of the structure may appear on the map.

Further, in the present example, the correspondence relationship between the degree of divergence and the gradation value in each of the structural abnormality degree maps 51A to 51F of the first to sixth layer boundaries is changed for each map according to the type of disease selected by the user. In this case, a relationship between the type of disease and the gamma value in the structural abnormality degree map for each boundary (information indicating the correspondence relationship between the degree of divergence and the gradation value in the present example) may be stored in advance in the storage device 24 as a look-up table. In the present example, the type of disease is selected via a box 54. When the box 54 is selected, a pull-down menu in which names of a plurality of diseases are listed is expanded. By selecting one of the names based on the operation, the structural abnormality degree maps 51A to 51F that reflect the gamma value according to the type of the disease are displayed on the screen. For example, in a retinal vein occlusion (RVO), since the structure of the entire retina is greatly disrupted, when RVO is selected, the sensitivity of each of the structural abnormality degree maps 51A to 51F may be reduced than usual. As a result, it is considered to easily recognize the whole picture of the abnormality of the structure caused by RVO.

Further, when the type of disease can be selectable as described above, any one or more of the structural abnormality degree maps 51A to 51F may be highlight displayed according to the selected type of disease. For example, when a central serous chorioretinopathy (CSC) is selected, the maps corresponding to each of the IS/OS and RPE/BM, which are important in the diagnosis of CSC, may be highlighted. By doing so, the amount of information that the user should check can be suitably reduced. Note that, various modes of highlight displaying can be considered. As an example, a frame line of the map to be highlight displayed may be highlighted by changing to a thick line.

Further, the structural abnormality degree maps 51A to 51F based on the two-dimensional distribution of the degree of divergence of the subject eye, which are illustrated as an example in FIG. 11, have an abnormality in the vicinity of the fovea. In FIG. 11, on some maps, the range having a high degree of divergence in the vicinity of the fovea is clearly wider as compared with the size of the fovea, so it is possible to easily recognize an abnormality. However, when the range having an abnormality is narrower compared to that in the example in FIG. 11 and overlaps with the fovea since the fovea is a tissue that originally tends to have a high degree of divergence, it may be difficult for the user to recognize the abnormality of the structure by using the structural abnormality degree map based on the two-dimensional distribution of the degree of divergence. In contrast to this, instead of the structural abnormality degree map based on the two-dimensional distribution of the degree of divergence, a difference map based on the two-dimensional distribution of the degree of divergence of the subject eye and the two-dimensional distribution of the degree of divergence in the normal eye may be displayed. The two-dimensional distribution of the degree of divergence in the normal eye may be created by collecting a plurality of three-dimensional OCT data in the normal eye. The difference map may be generated for each boundary. In the difference map, there is a possibility that the structural abnormality can be depicted more accurately when the tissue that originally tends to have a high degree of divergence and the abnormality overlap with each other.

Further, when there is a site in which the degree of divergence thereof is equal to or higher than the threshold value (hereinafter it is referred to as "abnormal site") in the tissue shown in the ophthalmic image (the three-dimensional tomographic image in the present embodiment), the CPU 23 displays a tomographic image (at least one of the two-dimensional tomographic image and the three-dimensional tomographic image) or an enlarged image of the abnormal site on the display device 28. In FIG. 11, the tomographic image 55 is illustrated. Specifically, of the plurality of two-dimensional tomographic images constituting the three-dimensional tomographic image, the CPU 23 of the present embodiment displays the tomographic image having the highest degree of divergence or the tomographic image having the degree of divergence equal to or higher than the threshold value, on the display device 28. In the present example, as illustrated in FIG. 11, the tomographic image 55 is displayed together with the structural abnormality degree maps 51A to 51F. Thereby, the user can immediately check the actual structure of the area having a high degree of divergence in the structural abnormality degree maps 51A to 51F. Further, in the present example, the graphic 56 indicating the acquisition position of the tomographic image 55 is displayed on either the structural abnormality degree maps 51A to 51F and the front image 52. As a result, the user can easily recognize the place where there is a possibility of the structural abnormality.

Note that, the tomographic image simultaneously displayed with the structural abnormality degree maps 51A to 51F may be changeable. For example, the tomographic image at any acquisition position may be displayed. Further, the tomographic image having the degree of abnormality of the structure equal to or less than the threshold value (for example, the tomographic image acquired on the line indicated by reference numeral 57 in FIG. 11) may be displayed together with the tomographic image 55 or by switching to the tomographic image 55.

Further, by identifying the layer or the layer boundary, each of the layers or the layer boundaries identified in the tomographic image may be displayed in an identifiable manner. Identification information for identifying each of the layers or layer boundaries may be assigned to the tomographic image 55 illustrated in FIG. 11. For example, lines highlighting the layer boundaries may be superimposed on the positions of the first to sixth layer boundaries in the tomographic image 55. Further, texts associated with each of the first to sixth layer boundaries in the tomographic image 55 may be displayed.

Re-Imaging

The processing can be similarly executed when the ophthalmic image capturing device 11B executes the ophthalmic image processing. Further, for example, in the display mode in FIG. 11, the plurality of structural abnormality degree maps 51A to 51F may be displayed on the check screen.

The controller may execute processing of outputting an imaging instruction for imaging the site having the degree of abnormality of the structure equal to or higher than the threshold value on the structural abnormality degree map to the ophthalmic image capturing device. Further, the controller may execute processing of displaying the tomographic image or an enlarged image of the site having the degree of abnormality of the structure equal to or higher than the threshold value on the display device. In this case, the image of the site having a high degree of abnormality of the structure is appropriately checked by the user.

Note that, when the controller outputs the imaging instruction for imaging the site having the degree of abnormality of the structure equal to or higher than the threshold value, an instruction may be output to capture the tomographic image of the site having the degree of abnormality of the structure equal to or higher than the threshold value with higher image quality. For example, an instruction for acquiring a higher resolution tomographic image may be output. Further, an instruction may be output in which the tomographic image of the site having the degree of abnormality of the structure equal to or higher than the threshold value is captured a plurality of times and an average added image of the plurality of captured tomographic images is acquired. In this case, the ophthalmic image of the site having a high degree of abnormality of the structure is acquired with high image quality.

Modification Example

The techniques disclosed in the above embodiments are merely examples. Therefore, it is possible to modify the techniques exemplified in the above embodiments.

Follow-Up Observation

Using the structural abnormality degree map based on ophthalmic images captured at different dates and times for the same subject eye (hereinafter referred to as a plurality of structural abnormality degree maps in a time series), a display for follow-up the observation may be performed by the ophthalmic image processing device 23. For example, the plurality of structural abnormality degree maps in a time series may include a plurality of structural abnormality degree maps generated for each layer or each boundary, and the plurality of time series structural abnormality degree maps may be displayed for each of the layers or each of the boundaries. At the same time, a trend graph showing the change in degree of abnormality for each layer or each boundary may be displayed.

At this time, the difference map based on two time series structural abnormality degree maps may be generated and displayed. The two-dimensional distribution of the increase or decrease in the degree of abnormality of the structure may be displayed as the difference map. By using the difference map, it is possible for the user to easily check the time change of the degree of abnormality of the structure for each position.

Selectively Display One or More Structural Abnormality Degree Maps for Each Layer According to Type of Disease In the above example, a display mode is shown in which all of the plurality of structural abnormality degree maps for each layer or each boundary generated from the three-dimensional tomographic image are simultaneously displayed on the display device. However, the display mode of the structural abnormality degree map is not necessarily limited to this. For example, of the plurality of structural abnormality degree maps generated from the three-dimensional tomographic images, one or more structural abnormality degree maps may be selectively displayed according to the type of disease. At this time, there may be two or more structural abnormality degree maps according to the type of disease, and in this case, two or more structural abnormality degree maps according to the type of disease may be simultaneously displayed. By doing so, information to be checked by the user can be suitably reduced.

Search/Identification of Type of Disease Utilizing Structural Abnormality Degree Map In the above example, the type of disease is manually selected by the user via the box 54, However, the present disclosure is not necessarily limited to this and may be automatically selected (classified). For example, as a result of the automatic diagnosis, information indicating the type of disease may be acquired. At this time, the automatic diagnosis may be executed based on the structural abnormality degree map. For example, by inputting the structural abnormality degree map into the mathematical model that outputs an automatic diagnosis result related to a disease of the subject eye, the information indicating the type of the disease may be acquired. The mathematical model may be learned by using the structural abnormality degree map and the diagnostic result (for example, the type of disease) which is the correct answer data of each structural abnormality degree map, as teacher data. Since the structural abnormality degree map is a map that extracts only the structural abnormality of the three-dimensional tomographic image (information that is efficiently compressed by focusing on the structural abnormality), it is considered that the result focusing on the structural abnormality can be further obtained as compared with the case of obtaining the automatic diagnosis result based on the three-dimensional tomographic image. Further, since the information of the structural abnormality degree map is compressed as compared with the three-dimensional tomographic image, it is possible to acquire the automatic diagnosis result at a higher speed by utilizing the structural abnormality degree map. Therefore, as in the above-described embodiment and example, of the plurality of structural abnormality degree maps generated for each layer or each boundary, the structural abnormality degree map may be utilized for the automatic diagnosis of the subject eye, for the purpose other than specifying the map to select display or highlight display.

Further, in the field of image diagnosis, a technique for searching for similar cases based on an image of a person to be examined is known. By inputting a search query into a similar case search database, similar case data corresponding to the search query can be obtained. The similar case data may be at least one of the ophthalmic image in a similar case, the diagnosis result for a similar case, the follow-up observation result in a similar case, and the like. The structural abnormality degree map may be utilized as the search query in such a similar case search. When the structural abnormality degree map is utilized as the search query, it is considered that the similar case can be obtained faster than when the three-dimensional tomographic image is input as the search query.

What is claimed is:

1. An ophthalmic image processing device that processes an ophthalmic image of a subject eye, comprising:
   a controller comprising a processor and programming configured to:
      acquire an ophthalmic image including a tomographic image of a plurality of tomographic planes in a fundus of the subject eye, wherein the tomographic image is an optical coherence Tomography (OCT) image;
      acquire a probability distribution for identifying two or more layers in the fundus and/or boundaries of the layers included in a plurality of layers and/or layer boundaries in the tomographic image, by inputting the ophthalmic image into a mathematical model trained with using a machine learning algorithm;
      generate a structural abnormality degree map showing a two-dimensional distribution of a degree of abnormality of a structure in the fundus, for each of the two or more layers and/or layer boundaries, based on the probability distribution; and
      simultaneously display two or more structural abnormality degree maps generated for each of the two or more layers and/or layer boundaries side by side on a display device,
   wherein a correspondence relationship between a gradation value of each pixel and the degree of abnormality of the structure in the structural abnormality degree map is variable for each structural abnormality degree map generated for each layer and/or layer boundary, or the correspondence relationship differs according to the structural abnormality degree map generated for each layer and/or layer boundary.

2. The ophthalmic image processing device according to claim 1,
   wherein the controller selects a type of disease and sets the correspondence relationship for each layer and/or layer boundary according to the selected type of disease.

3. The ophthalmic image processing device according to claim 1,
   wherein the controller sets the correspondence relationship for each layer and/or layer boundary according to a noise level in the ophthalmic image.

4. The ophthalmic image processing device according to claim 1,
   wherein the controller is configured to:
      further acquire a front image of the subject eye corresponding to the structural abnormality degree map; and
      display the front image together with the two or more structural abnormality degree maps on the display device.

5. The ophthalmic image processing device according to claim 4,
   wherein the controller is configured to:
      acquire an image showing a distribution of blood vessels as the front image; and
      simultaneously display the two or more structural abnormality degree maps together with the front image of a layer and/or layer boundary identical to at least one of the structural abnormality degree maps.

6. An ophthalmic image processing device that processes an ophthalmic image of a subject eye, comprising:
   a controller comprising a processor and programming configured to:
      acquire an ophthalmic image including a tomographic image of a plurality of tomographic planes in a subject eye, wherein the tomographic image is an optical coherence Tomography (OCT) image;
      acquire a probability distribution for identifying two or more tissues included in a plurality of tissues in the tomographic image, by inputting the ophthalmic image into a mathematical model trained with using a machine learning algorithm;
      generate a structural abnormality degree map showing a two-dimensional distribution of a degree of abnormality of a structure in the tissue, for each of the two or more tissues, based on the probability distribution; and simultaneously display two or more structural abnormality degree maps generated for each of the two or more tissues side by side on a display device;

wherein the controller is configured to generate the structural abnormality degree map showing a two-dimensional distribution of a degree of abnormality of the structure, based on a degree of divergence between the probability distribution acquired for the subject eye and the probability distribution output in a case where a layer or a layer boundary is accurately identified.

7. The ophthalmic image processing device according to claim 6, wherein the controller is configured to generate the structural abnormality degree map in which a difference between the degree of divergence and a degree of divergence in a normal eye is set to the degree of abnormality of the structure.

8. The ophthalmic image processing device according to claim 1, wherein the mathematical model is trained with using a training data set in which:

an ophthalmic image including a tomographic image of a plurality of tomographic planes in a subject eye captured ago is used as an input side; and data indicating a layer or a layer boundary in the tomographic image on the input side is used as an output side.

9. An ophthalmic image processing method executed by an ophthalmic image processing device that processes an ophthalmic image of a subject eye, in which an ophthalmic image processing program is executed by a controller, comprising a processor and programming, of the ophthalmic image processing device to cause the ophthalmic image processing device to execute:

an image acquisition step of acquiring an ophthalmic image including a tomographic image of a plurality of tomographic planes in a fundus of the subject eye as an ophthalmic image captured by an ophthalmic image capturing device, wherein the tomographic image is an optical coherence Tomography (OCT) image;

an acquisition step of acquiring a probability distribution for identifying two or more layers in the fundus and/or boundaries of the layers included in a plurality of layers and/or layer boundaries in the tomographic image, by inputting the ophthalmic image into a mathematical model trained with using a machine learning algorithm;

a structural abnormality degree map generation step of generating a structural abnormality degree map showing a two-dimensional distribution of a degree of abnormality of a structure in the fundus, for each of the two or more layers and/or layer boundaries, based on the probability distribution; and a display step of simultaneously displaying two or more structural abnormality degree maps generated for each of the two or more layers and/or layer boundaries side by side on a display device;

wherein a correspondence relationship between a gradation value of each pixel and the degree of abnormality of the structure in the structural abnormality degree map is variable for each structural abnormality degree map generated for each layer and/or layer boundary, or the correspondence relationship differs according to the structural abnormality degree map generated for each layer and/or layer boundary.

10. The ophthalmic image processing device according to claim 1, wherein the processor is a CPU or GPU.

\* \* \* \* \*